United States Patent
Wright et al.

(10) Patent No.: US 11,427,835 B2
(45) Date of Patent: Aug. 30, 2022

(54) VECTORS COMPRISING STUFFER/FILLER POLYNUCLEOTIDE SEQUENCES AND METHODS OF USE

(71) Applicant: THE CHILDREN'S HOSPITAL OF PHILADELPHIA, Philadelphia, PA (US)

(72) Inventors: J. Fraser Wright, Philadelphia, PA (US); Olga Zelenaia, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 481 days.

(21) Appl. No.: 14/776,630

(22) PCT Filed: Mar. 14, 2014

(86) PCT No.: PCT/US2014/028911
§ 371 (c)(1),
(2) Date: Sep. 14, 2015

(87) PCT Pub. No.: WO2014/144486
PCT Pub. Date: Sep. 18, 2014

(65) Prior Publication Data
US 2016/0032319 A1    Feb. 4, 2016

Related U.S. Application Data

(60) Provisional application No. 61/799,342, filed on Mar. 15, 2013.

(51) Int. Cl.
*C12N 15/864* (2006.01)
*C12N 15/86* (2006.01)
*A61K 48/00* (2006.01)
*C12N 7/00* (2006.01)

(52) U.S. Cl.
CPC .......... *C12N 15/86* (2013.01); *A61K 48/0025* (2013.01); *A61K 48/0091* (2013.01); *C12N 7/00* (2013.01); *C12N 2750/14121* (2013.01); *C12N 2750/14132* (2013.01); *C12N 2750/14141* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| 6,294,379 B1 * | 9/2001 | Dong | C07K 14/4712 |
| | | | 435/320.1 |
| 6,521,426 B1 | 2/2003 | Ciliberto et al. | |
| 2007/0243168 A1* | 10/2007 | Kay | A61K 48/0058 |
| | | | 424/93.2 |

FOREIGN PATENT DOCUMENTS

| RU | 2457252 C2 | 7/2012 |
| WO | 2003/104485 A2 | 12/2003 |
| WO | 2007/148971 A2 | 12/2007 |
| WO | 2008/016391 A2 | 2/2008 |
| WO | 2012/158757 A1 | 11/2012 |
| WO | 2013123503 A1 | 8/2013 |

OTHER PUBLICATIONS

Grieger, J. et al., J. Virol., 2005, vol. 79: pp. 9933-9944.*
Dong, J. et al., Hum. Gene Ther., 1996, vol. 7: pp. 2101-2112.*
Rabinowitz, J. et al., J. Virol., 2001, vol. 76: pp. 791-801.*
Promega Corp., pSP73 vector technical bulletin, Sep. 2006, 9 pages.*
Zelenaia, O., et al., Inverted Terminal Repeat Read-Through and Reverse Packaging: Mechanisms of Occurence and Strategies to Minimize DAN Impurities in Recombinant AAV, Human Gene Therapy, 2012, 23(10):A49-A50.
Zelenaia, O., et al., Characterization of Residual Plasmid DNA Impurities in Recombinant AAV; Correlation with Size of Transgene Expression Cassette, Molecular Therapy, 2012, 20(suppl. 1):S143.
Wright, J.F. et al., Manufacturing and Characterizing AAV-Based Vectors for Use in Clinical Studies, Gene Therapy, 20008, 15(11):840-848.
Chadeuf G. et al., Evidence for Encapsidation of Prokaryotic Sequences during Recombinant Adeno-Associated Virus Production and Their in Vivo Persistence after Vector Delivery, Molecular Therapy, 2005, 12(4):744-753.
Hauck B. et al., Undetectable Transcription of cap in a Clinical AAV Vector: Implications for Preformed Capsid in Immune Responses, Molecular Therapy, 2009, 17(1 ):144-152.
Wright J.F., Review Transient Transfection Methods for Clinical Adena-Associated Viral Vector Production, Human Gene Therapy, 2009, 20:698-706.
Wang, et al., AAV Vectors Containing rDNA Homology Display Increased Chromosomal Integration and Transgene Persistence, Mol. Ther., 2012, 20(10):1902-11.
PCT International Application No. PCT/US2014/028911, International Search Report & Written Opinion, dated Sep. 19, 2014.

(Continued)

*Primary Examiner* — Michael D Burkhart
(74) *Attorney, Agent, or Firm* — Robert M. Bedgood; Pillsbury Winthrop Shaw Pittman LLP

(57) ABSTRACT

Recombinant viral vectors such as AAV vectors designed with expression cassettes that approach the natural packaging capacity of the virus, such as AAV are provided. The recombinant viral vectors reduce residual plasmid DNA impurities.

33 Claims, 11 Drawing Sheets

(56) References Cited

OTHER PUBLICATIONS

Zelenaia, O., et al., Inverted Terminal Repeat Read-Through and Reverse Packaging: Mechanisms of Occurence and Strategies to Minimize DNA Impurities in Recombinant AAV, Human Gene Therapy, 2012, 23(10):A49-A50, XP009191572, & Collaborative Congress of the European Society of Gene and Cell Therapy/French Society of Cell and G; Versailles, France, Oct. 25-29, 2012.

Zelenaia, O., et al., Characterization of Residual Plasmid DNA Impurities in Recombinant AAV; Correlation with Size of Transgene Expression Cassette, Molecular Therapy, 2012, 20(suppl. 1):S143, XP009191575, & 15th Annual Meeting of the American Society of Gene and Cell Therapy (ASGCT); Philadelphia, PA, USA; May 16-19, 2012.

Nowrouzi, A., et al., Dissecting rAAV Integration Frequency in Non-Human Primates by Deep Sequencing, Molecular Therapy, 2010, 18(Supplement 1):S117.

Palfi, A., et al., Adeno-Associated Virus-Mediated Rhodopsin Replacement Provides Therapeutic Benefit in Mice with a Targeted Disruption of the Rhodopsin Gene, 2010, Human Gene Therapy, 21:311-323.

\* cited by examiner

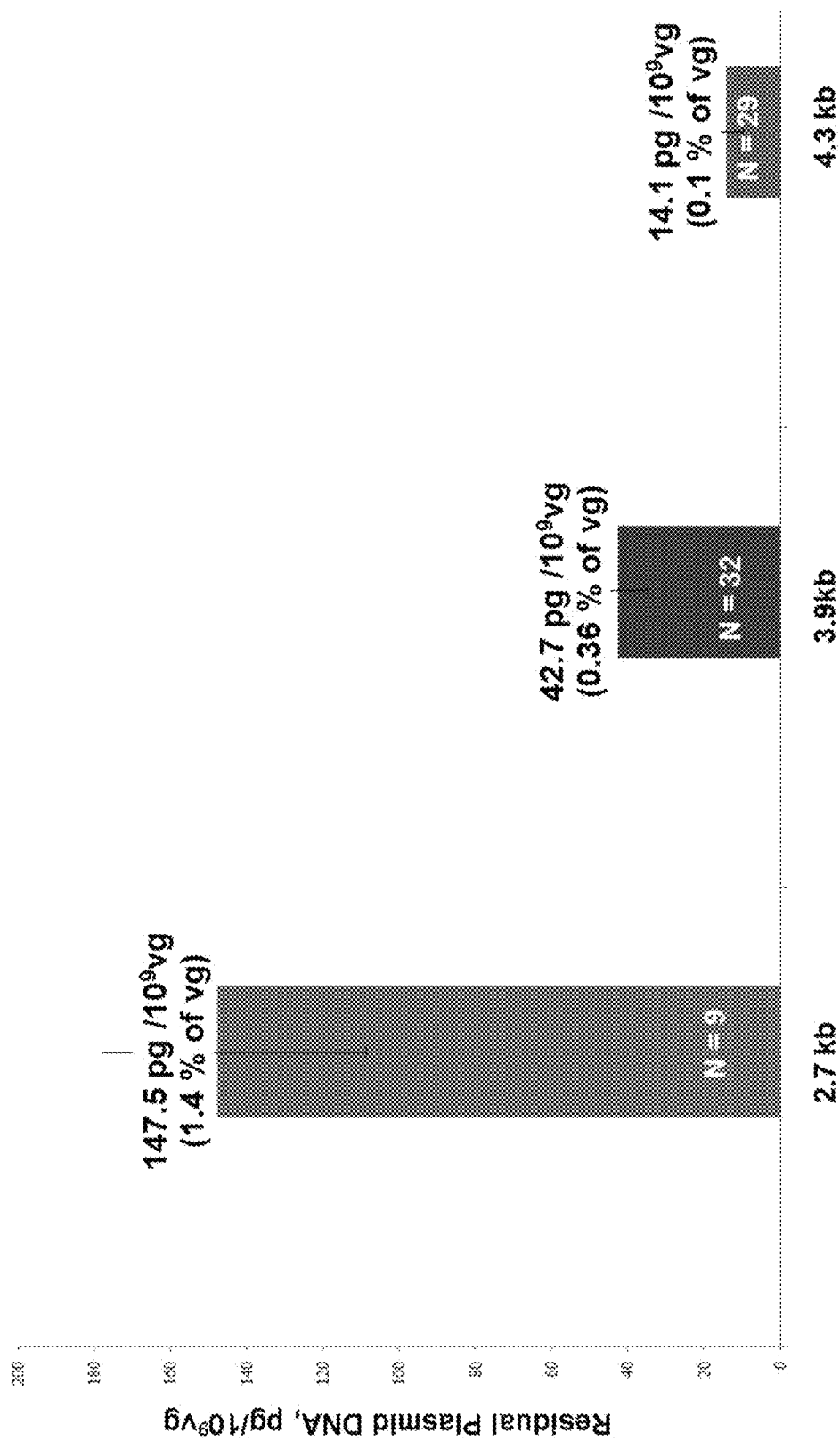
Figure 1: Correlation of residual plasmid DNA levels with rAAV vector genome size

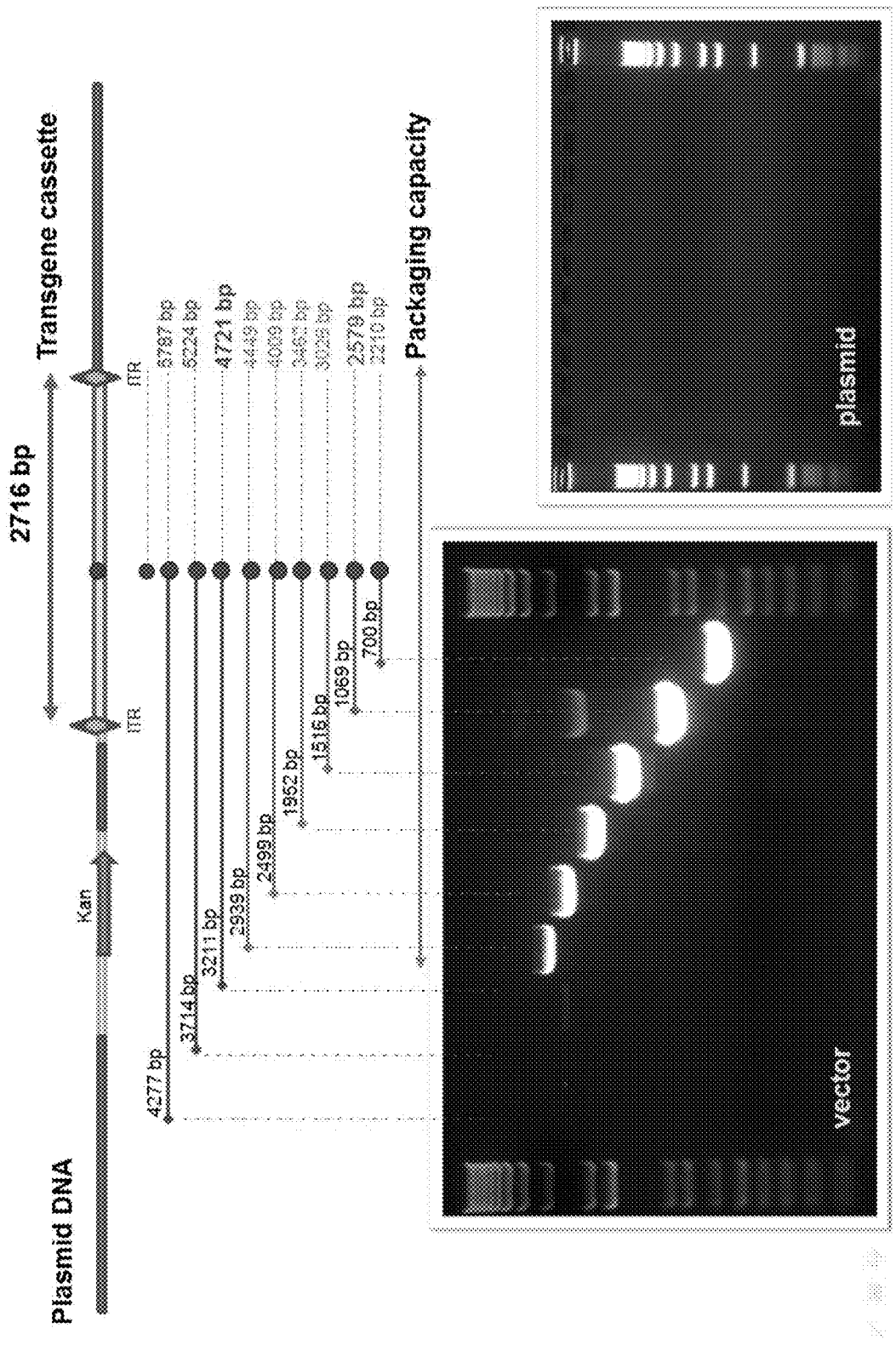
Figure 2A: PCR on Vector with Short Transgene Cassette (2.7kb) before DNase treatment

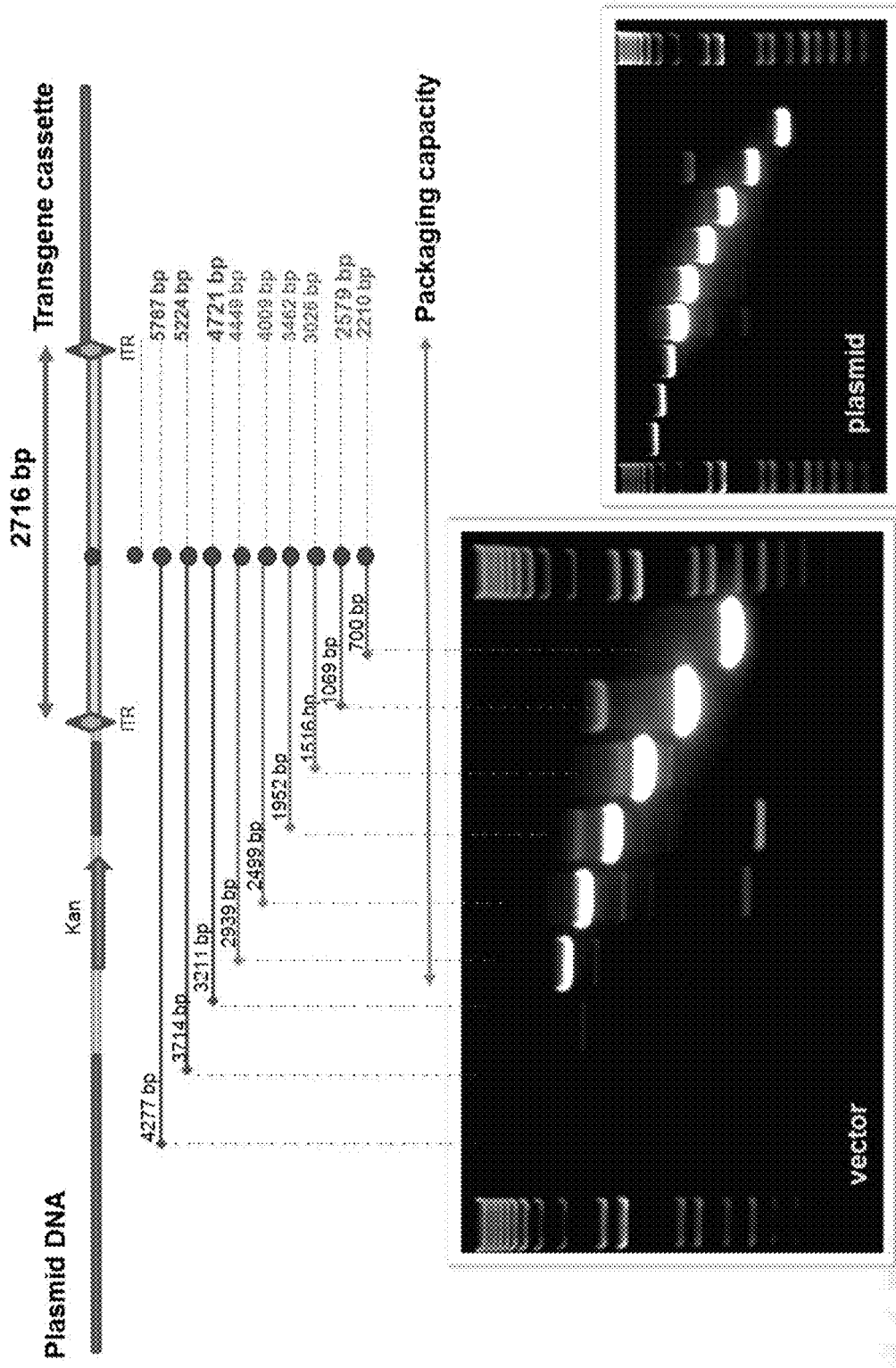
Figure 2B: PCR on Vector with Short transgene cassette (2.7kb) after DNase treatment and DNA purification with High Pure Viral Nucleic Acid Kit (Roche)

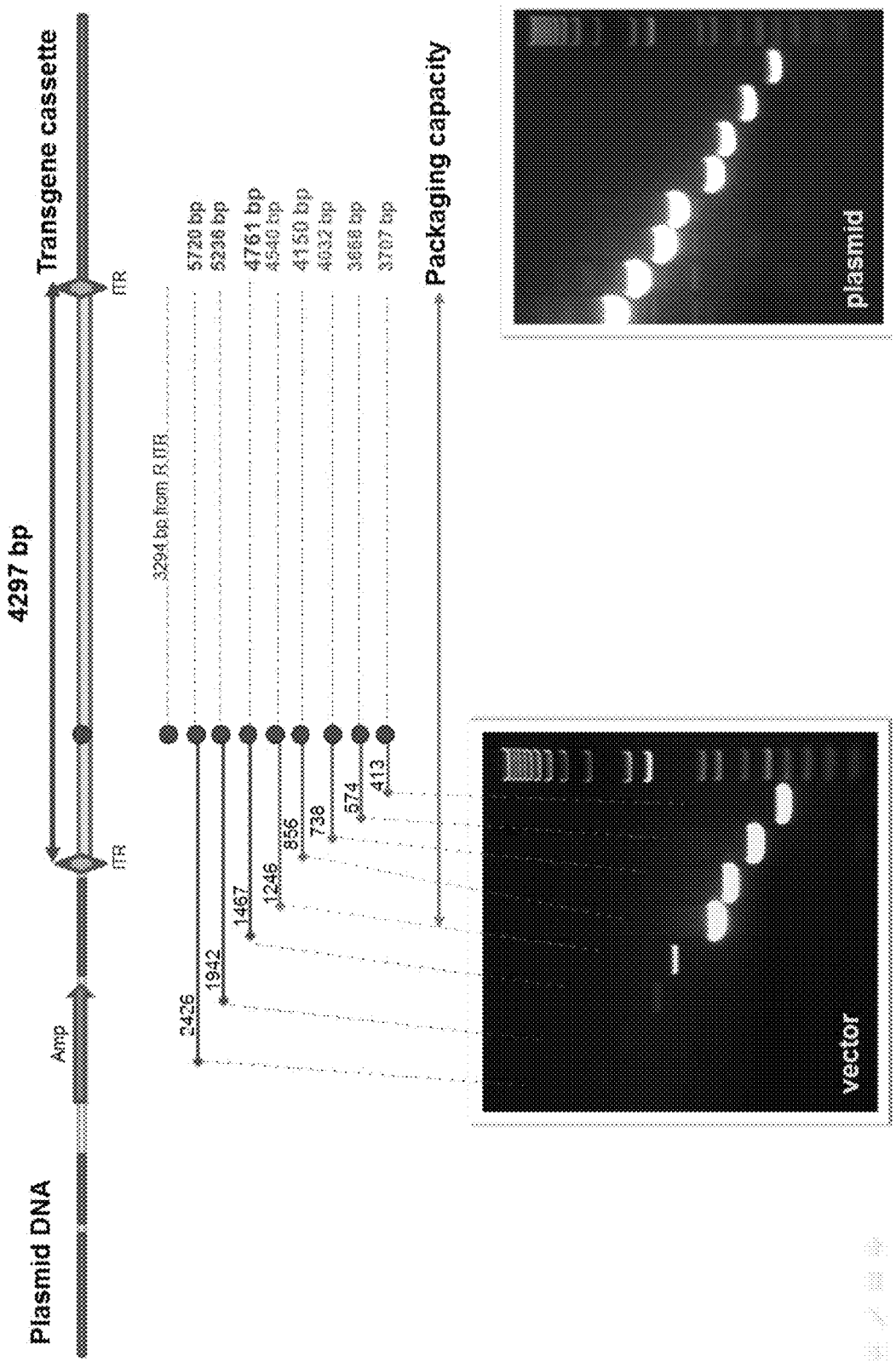
Figure 2C: PCR on Vector with Long Transgene Cassette (4.3kb) before DNase treatment

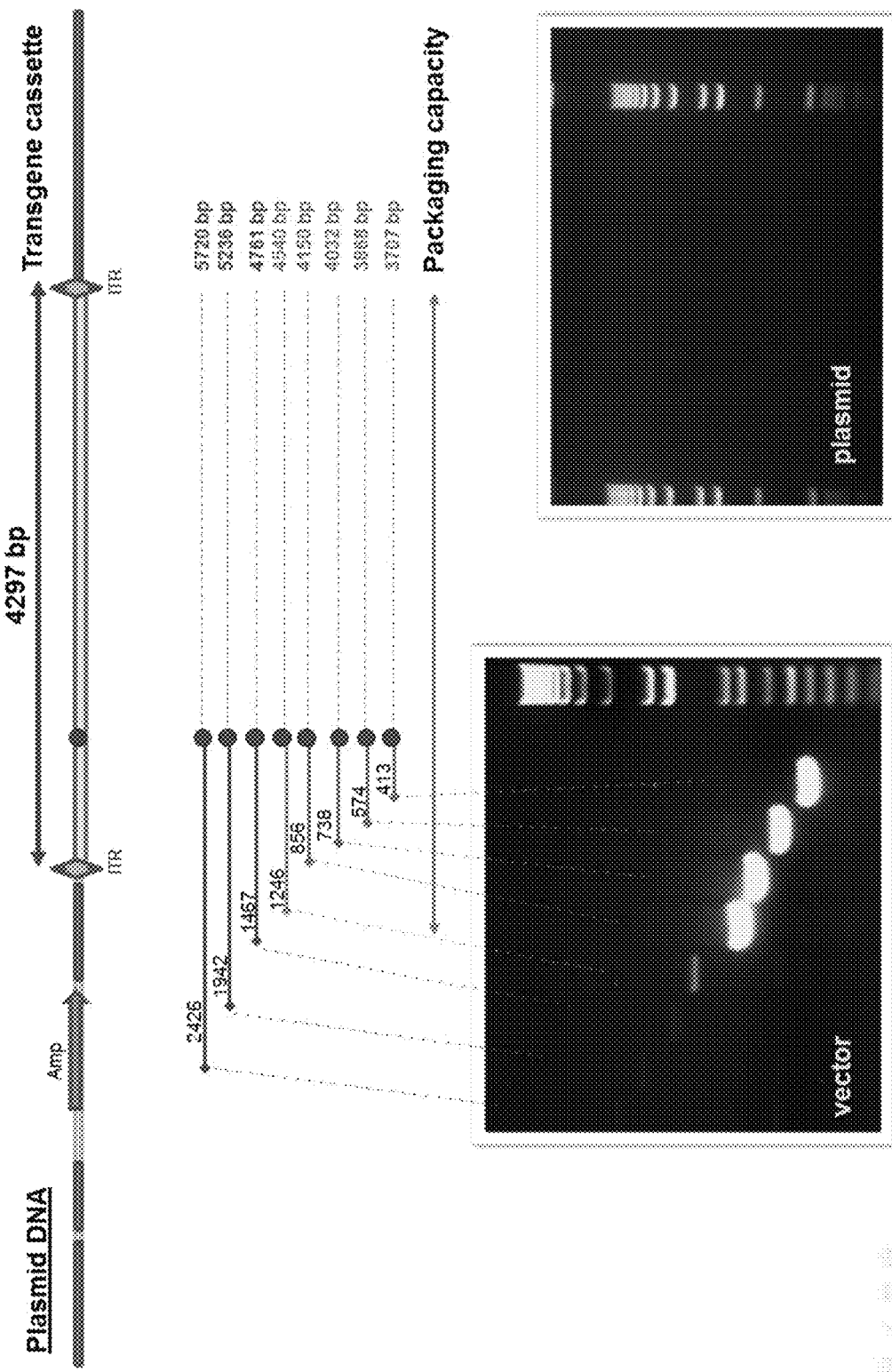
Figure 2D: PCR on Vector with Long transgene cassette (4.2kb) after DNase treatment and DNA purification with High Pure Viral Nucleic Acid Kit (Roche)

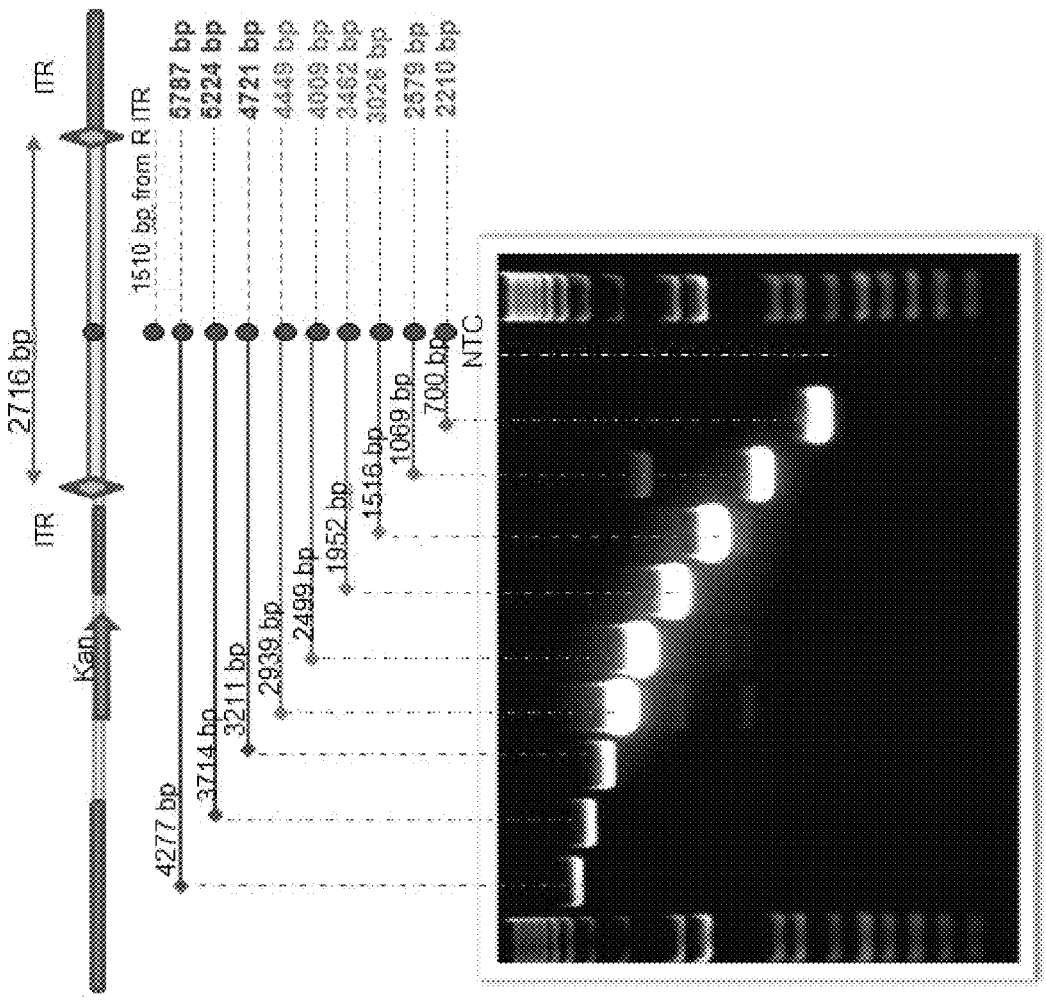
Figure 3A: Plasmid with Transgene cassette (2.7kb)

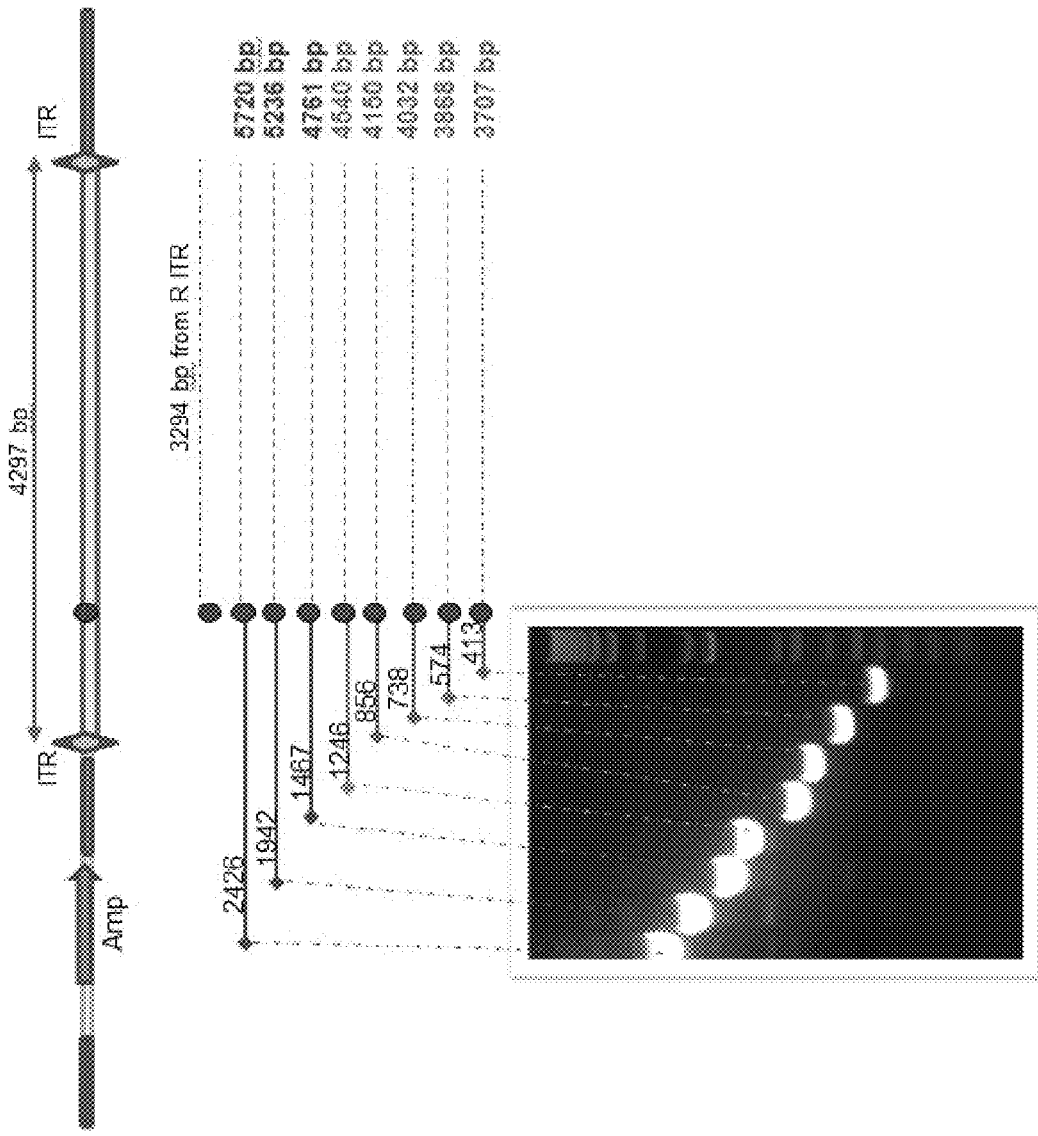
Figure 3B: Plasmid with Transgene cassette (4.3kb)

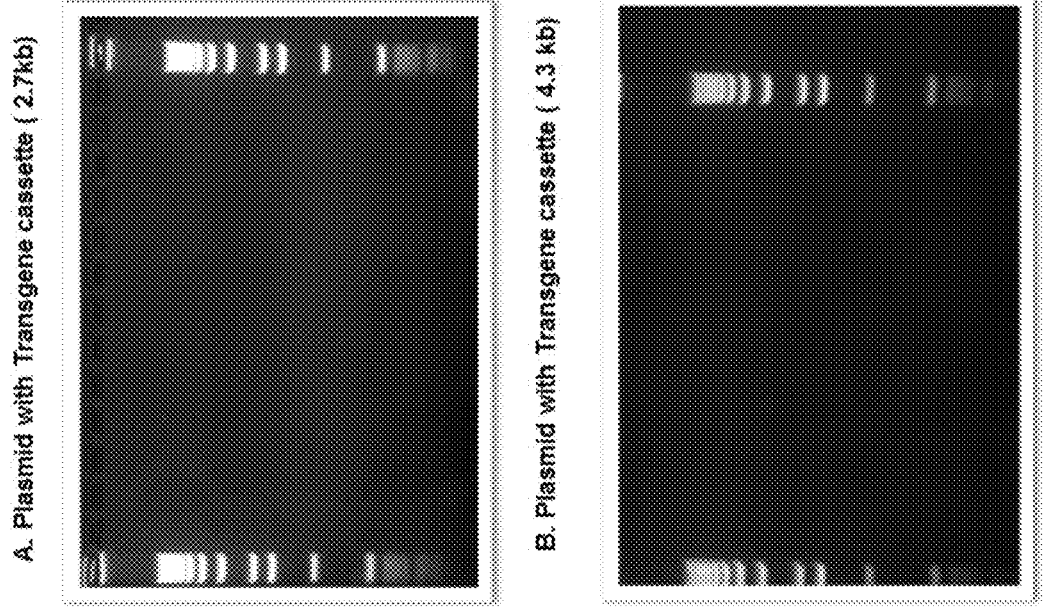
Figure 3C: After DNase treatment of plasmid samples with DNase

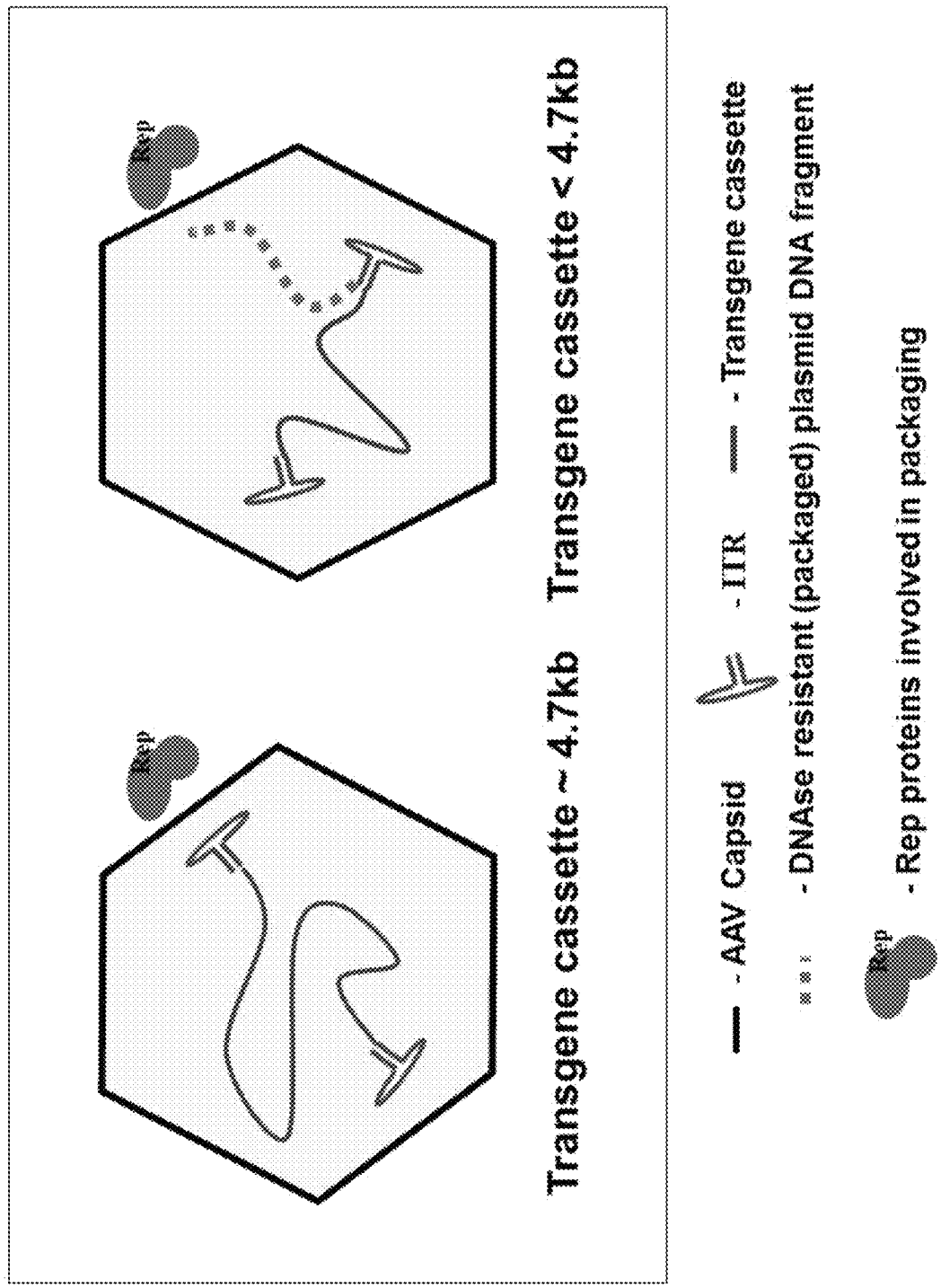
Figure 4: Diagram showing encapsidation of plasmid DNA in vectors with Short Transgene Cassette.

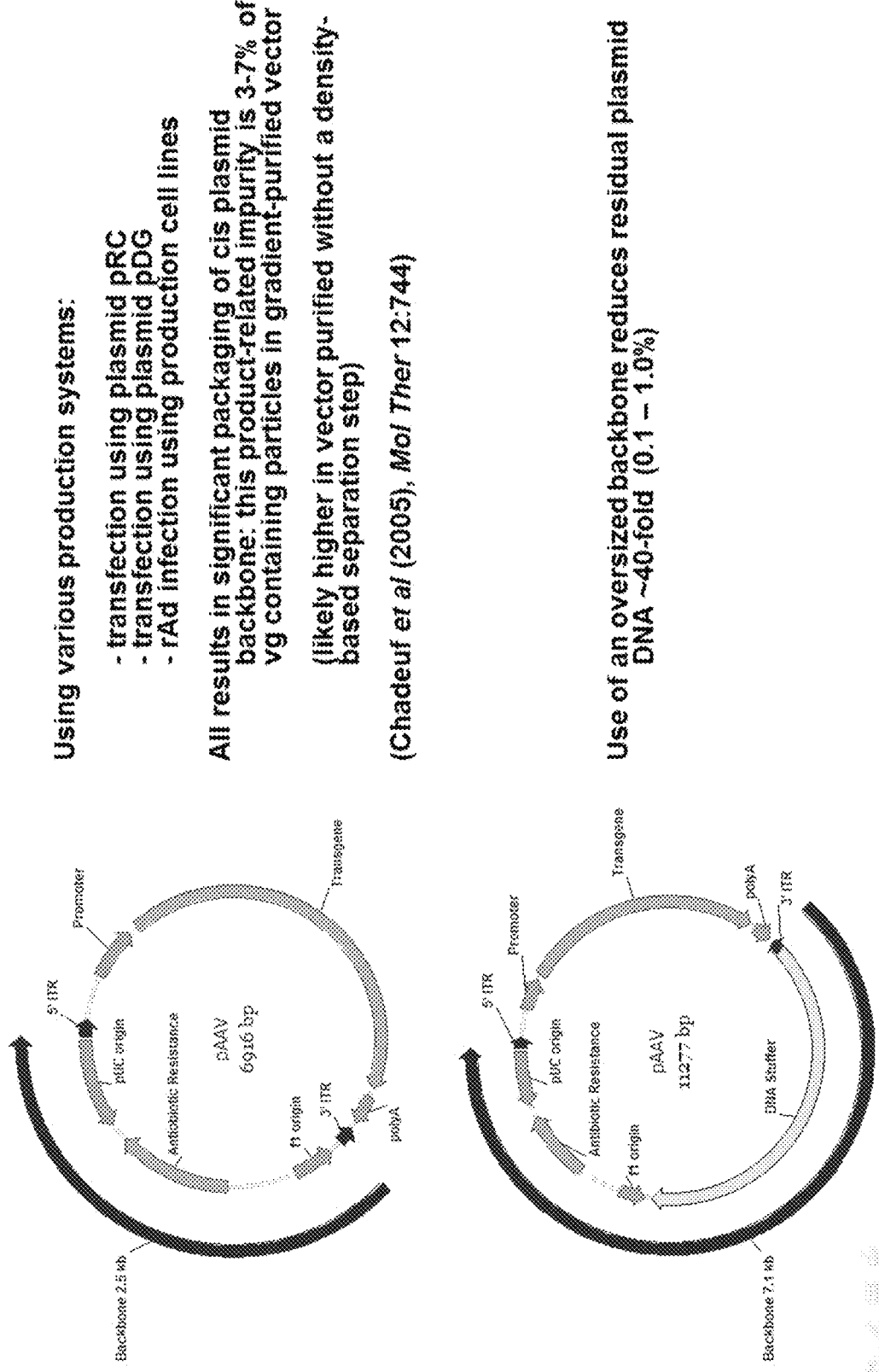
Figure 5: Oversized plasmid backbone (7.1Kb) exceeding the AAV packaging limit markedly reduces non-vector DNA packaging.

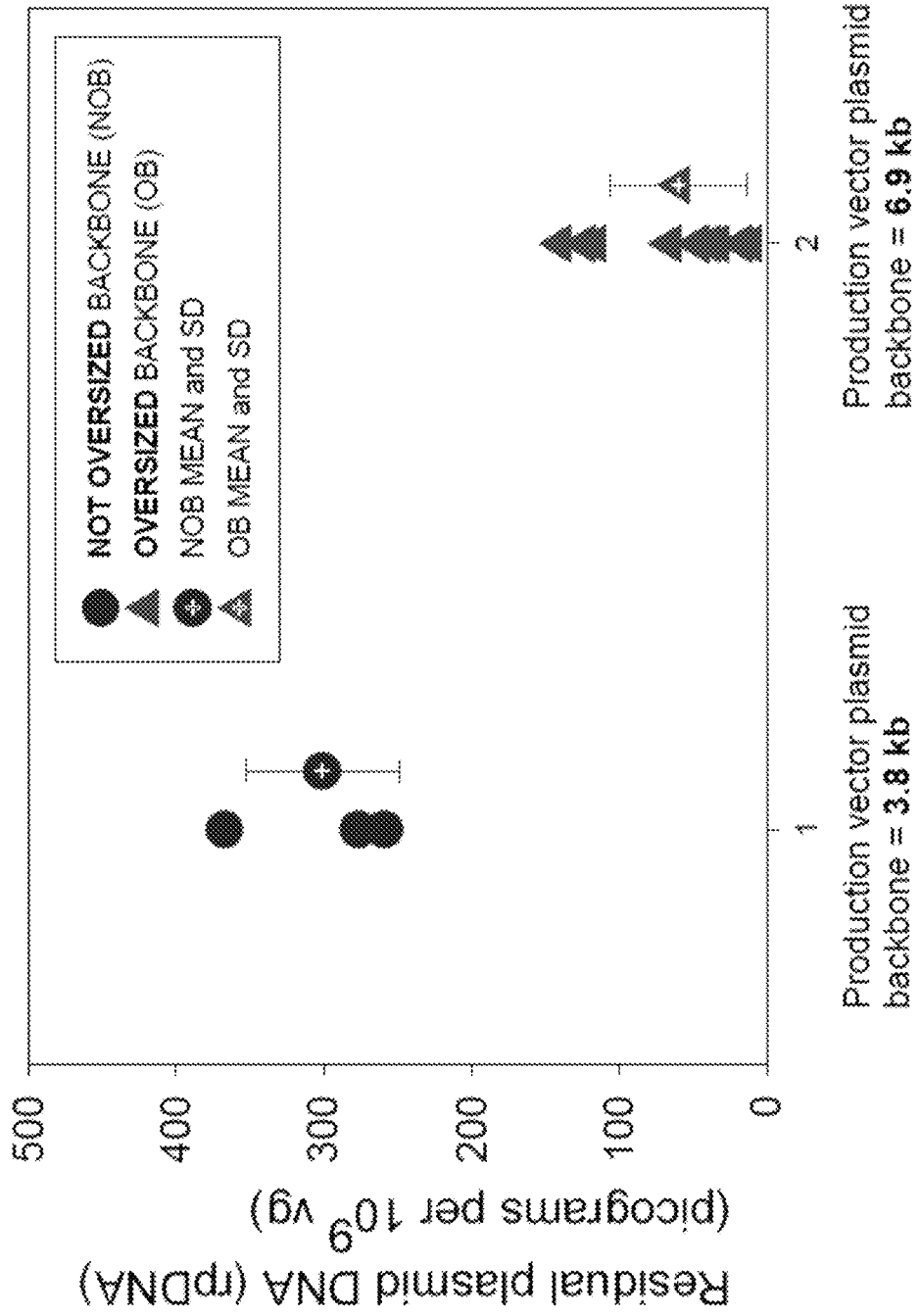
Figure 6: Residual plasmid DNA in purified AAV vectors made with vector plasmids containing non oversized[1] (red) versus oversized (green) backbones
[1] Oversized; i.e., larger than the packaging capacity of Adeno associated virus (approx.. 4.7kb).

VECTORS COMPRISING STUFFER/FILLER POLYNUCLEOTIDE SEQUENCES AND METHODS OF USE

RELATED APPLICATION INFORMATION

This application is the National Phase of International Application No. PCT/US2014/028911, filed Mar. 14, 2014 which designated the U.S. and that International Application was published under PCT Article 21(2) in English, and claims priority to application Ser. No. 61/799,342, filed Mar. 15, 2013, all of which applications are expressly incorporated herein by reference in their entirety.

INTRODUCTION

Recombinant adeno-associated virus (AAV) vectors have shown excellent therapeutic promise in several early phase clinical trials by multiple groups reported to date. Development of this new class of biologic product towards advanced clinical studies and eventual licensure will involve further improvements in vector characterization and quality control methods, including a better understanding of how vector design and manufacturing process parameters affect impurity profiles in the purified clinical grade vectors. Removal of DNA impurities in AAV vectors is complicated by the fact that even with efficient nuclease treatment to remove accessible nucleic acids during vector purification, fragments of DNA may be packaged and thus resistant to nuclease treatment performed in a manner to maintain vector particle integrity.

An important objective in the design of rAAV production systems is to characterize and implement strategies to minimize/control the generation of vector-related impurities, including wild-type/pseudo wild-type AAV species (wtAAV), AAV-encapsidated residual DNA impurities, and empty capsids. Such product-related impurities closely resemble the vector itself, and cannot easily be separated from bona fide vectors during the purification process. Non vector DNA impurities have been reported at an abundance in the range from 1 to 8% of total DNA in purified vector particles (Smith P H Wright J F. Qu G. et al 2003, *Mo. Therapy*, 7:8348; Chadeuf G. Ciron C. Moullier P. Salvetti A., *Mo. Therapy* 2005, 12:744. Report from the CHMP gene therapy expert group meeting. European Medicines Agency EMEA/CHMP 2005, 183989/2004). A significant portion of the encapsidated residual DNA is derived from the ITR-containing vector plasmid template.

SUMMARY

In accordance with the invention, provided are recombinant vector plasmids and virus particles that include (encapsidate, package) vector genomes. In one embodiment, a recombinant vector plasmid includes a heterologous polynucleotide sequence and a filler or stuffer polynucleotide sequence.

In accordance with the invention, also provided are recombinant AAV vector plasmids and AAV particles that include (encapsidate, package) AAV vector genomes. In one embodiment, a recombinant AAV vector plasmid includes a heterologous polynucleotide sequence and a filler or stuffer polynucleotide sequence.

In various embodiments, a heterologous polynucleotide sequence has a length less than about 4.7 Kb. In particular aspects, the heterologous polynucleotide sequence has a length less than 4.7 Kb and is positioned within two adeno-associated virus (AAV) ITR sequences. In particular aspects, a filler or stuffer polynucleotide sequence has a length that when combined with the heterologous polynucleotide sequence the total combined length of the heterologous polynucleotide sequence and filler or stuffer polynucleotide sequence is between about 3.0-5.5 Kb, or between about 4.0-5.0 Kb, or between about 4.3-4.8 Kb.

Filler or stuffer polynucleotide sequences can be located in the vector at any desired position such that it does not prevent a function or activity of the vector. In one aspect, a filler or stuffer polynucleotide sequence is not positioned between a 5' and/or 3' ITR that flanks the respective 5' and/or 3' termini of a heterologous polynucleotide sequence. In another aspect, a filler or stuffer polynucleotide sequence is positioned within a 5' and/or 3' ITR that flanks the respective 5' and/or 3' termini of a heterologous polynucleotide sequence. In an additional aspect, a filler or stuffer polynucleotide sequence is positioned adjacent to 5' and/or 3' ITR that flanks the respective 5' and/or 3' termini of a heterologous polynucleotide sequence. In a further aspect, a filler or stuffer polynucleotide sequence is positioned within a heterologous polynucleotide sequence, e.g., analogous to an intron within a genomic nucleic acid.

Thus, in various embodiments, a filler or stuffer polynucleotide sequence is positioned within two adeno-associated virus (AAV) ITR sequences; a filler or stuffer polynucleotide sequence is positioned outside two adeno-associated virus (AAV) ITR sequences; or there are two filler or stuffer polynucleotide sequences, a first filler or stuffer polynucleotide sequence positioned within two adeno-associated virus (AAV) ITR sequences, and a second filler or stuffer polynucleotide sequence positioned outside two adeno-associated virus (AAV) ITR sequences.

In various additional aspects, a filler or stuffer polynucleotide sequence is a sequence between 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000 nucleotides in length.

In more particular aspects, a filler or stuffer polynucleotide sequence has a length that when combined with said heterologous polynucleotide sequence the total combined length of the heterologous polynucleotide sequence and filler or stuffer polynucleotide sequence is between about 3.0-5.5 Kb, between about 4.0-5.0 Kb, or between about 4.3-4.8 Kb, when positioned within two adeno-associated virus (AAV) ITR sequences. In other more particular aspects, a filler or stuffer polynucleotide sequence has a length greater than 4.7 Kb, between about 5.0-10.0 Kb, or between about 6.0-8.0 Kb, when positioned outside two adeno-associated virus (AAV) ITR sequences.

The invention further provides recombinant vector plasmids including a second (third, fourth, etc.) filler or stuffer polynucleotide sequence. In one embodiment, a first filler or stuffer polynucleotide sequence is positioned within two adeno-associated virus (AAV) ITR sequences, and a second filler or stuffer polynucleotide sequence is positioned outside the two adeno-associated virus (AAV) ITR sequences.

In one aspect, a filler or stuffer polynucleotide sequence is inert or innocuous and has no function or activity. In various particular aspects, a filler or stuffer polynucleotide sequence is not a bacterial polynucleotide sequence, a filler or stuffer polynucleotide sequence is not a sequence that encodes a protein or peptide, a filler or stuffer polynucleotide sequence is a sequence distinct from any of: the heterologous polynucleotide sequence, an AAV inverted terminal repeat (ITR) sequence, an expression control element, an origin of replication, a selectable marker or a poly-Adenine (poly-A) sequence.

In various additional particular aspects, a filler or stuffer polynucleotide sequence is an intron sequence that is related to or unrelated to the heterologous polynucleotide sequence. In particular aspects, the intron sequence is positioned within the heterologous polynucleotide sequence. In other particular aspects, the intron sequence is related to the heterologous polynucleotide sequence as the intron is in genomic DNA, such as the genomic DNA that encodes a protein which protein is also encoded by the heterologous polynucleotide sequence.

In invention recombinant vector (e.g., AAV) plasmids and virus (e.g., AAV) particles that include (encapsidate, package) recombinant vector (e.g., AAV) genomes, the heterologous polynucleotide sequence may or be transcribed and subsequently translated into a protein, or may be transcribed into a transcript that in itself has a function or activity. In one aspect, the heterologous polynucleotide sequence encodes a therapeutic protein. In particular aspects, the protein is a blood clotting factor (e.g., Factor XIII, Factor IX, Factor X, Factor VIII, Factor VIIa, or protein C), CFTR (cystic fibrosis transmembrane regulator protein), an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes, or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

In another aspect, the heterologous polynucleotide sequence encodes a therapeutic protein that in turn inhibits expression or function of an undesirable or aberrant (dysfunctional) protein present (endogenous) in a subject. In a further aspect, the heterologous polynucleotide sequence is a polynucleotide which, when transcribed, is transcribed into an inhibitory nucleic acid (e.g., inhibitory RNA). In more particular aspects, an inhibitory nucleic acid is a single-stranded sequence, or forms a double- or triple-stranded sequence. In additional more particular aspects, an inhibitory nucleic acid is a micro-RNA (miRNA), siRNA, shRNA, trans-splicing RNA, antisense RNA or triplex forming RNA.

In still other aspects, the heterologous polynucleotide sequence encodes a protein that in inhibits infection or provides resistance or protection against infection, for example, HIV infection. In a particular aspect, the protein is chemokine receptor CCR5.

In further more particular aspects, an inhibitory nucleic acid inhibits expression of: huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular oedma (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; mutant rhodopsin gene (RHO) in autosomal dominantly inherited retinitis pigmentosa (adRP); or the inhibitory nucleic acid binds to a transcript of any of the foregoing genes or sequences.

Invention recombinant vector (e.g., AAV) plasmids and virus (e.g., AAV) particles that include (encapsidate, package) recombinant vector (e.g., AAV) genome include additional elements that function in cis or in trans. In particular embodiments, a recombinant viral (e.g., AAV) vector and/or virus (e.g., AAV) particle that includes (encapsidate, package) recombinant vector (e.g., AAV) genome also has: one or more inverted terminal repeat (ITR) sequences that flank the 5' or 3' terminus of the heterologous polynucleotide sequence; an expression control sequence that drives transcription of the heterologous polynucleotide sequence (e.g., a promoter or enhancer that contributes to transcription of the heterologous polynucleotide sequence, such as a constitutive or regulatable control element, or tissue-specific expression control element); a poly-Adenine sequence located 3' of the heterologous polynucleotide sequence; a selectable marker (e.g., a protein that provides antibiotic resistance, such as Kanamycin resistance); and/or an origin of replication.

Invention recombinant vector (e.g., AAV) plasmids and virus (e.g., AAV) particles that include (encapsidate, package) recombinant vector (e.g., AAV) genome can be included within cells. In such embodiments, cells can comprise helper cells lysed to produce virus particles, or target cells in which it is desired to express the heterologous polynucleotide sequence.

Invention recombinant vector (e.g., AAV) plasmids and virus (e.g., AAV) particles that include (encapsidate, package) recombinant vector (e.g., AAV) genomes can be included within pharmaceutical compositions. Such compositions are useful for administration of recombinant vector (e.g., AAV) plasmids and virus (e.g., AAV) particles that include (encapsidate, package) recombinant vector (e.g., AAV) genomes to a subject.

Invention recombinant vector (e.g., AAV) plasmids and virus (e.g., AAV) particles that include (encapsidate, package) recombinant vector (e.g., AAV) genomes may be employed in various methods and uses. In one embodiment, a method is for delivering or transferring a heterologous polynucleotide sequence into a subject (e.g., mammal) or a cell of a subject (e.g., mammal), and includes administering a viral (e.g., AAV) particle, a plurality of viral (e.g., AAV) particles, or a pharmaceutical composition of a viral (e.g., AAV) particle or plurality of viral (e.g., AAV) particles to a subject (e.g., mammal) or a cell of the subject (e.g., mammal), thereby delivering or transferring a heterologous polynucleotide sequence into the subject (e.g., mammal) or cell of the subject (e.g., mammal). In another embodiment, a method is for treating a subject (e.g., mammal) deficient or in need of protein expression or function, or in need of reduced expression or function of an endogenous protein (e.g., an undesirable, aberrant or dysfunctional protein), that includes providing a viral (e.g., AAV) particle, a plurality of viral (e.g., AAV) particles, or a pharmaceutical composition of a viral (e.g., AAV) particle or plurality of viral (e.g., AAV) particles; and administering the viral (e.g., AAV) particle, plurality of viral (e.g., AAV) particles, or pharmaceutical composition of viral (e.g., AAV) particle or plurality of viral (e.g., AAV) particles to the subject (e.g., mammal), where the heterologous polynucleotide sequence is expressed in the mammal, or wherein the heterologous polynucleotide sequence encodes an inhibitory sequence or protein that reduces expression or function of an endogenous protein (e.g., an undesirable, aberrant or dysfunctional protein) in the subject (e.g., mammal).

Methods and uses for administration or delivery include any mode compatible with a subject. In particular embodiments, the viral (e.g., AAV) particle or plurality of viral (e.g., AAV) particles is administered or delivered intravenously, intraarterially, intramuscularly, subcutaneously, orally, by intubation, via catheter, dermally, intra-cranially, via inhalation, intra-cavity, or mucosally.

Subjects include mammals, such as humans and non-humans (e.g., primates). In particular embodiments, a subject would benefit from or is in need of expression of a heterologous polynucleotide sequence.

In accordance with the invention, methods of producing invention recombinant vector (e.g., AAV) plasmids and virus (e.g., AAV) particles that include (encapsidate, package) recombinant vector (e.g., AAV) genomes are provided. In one embodiment, a method of producing recombinant viral or AAV particles includes introducing into a packaging helper cell a recombinant vector (e.g., AAV) plasmid to produce a productive viral (e.g., AAV) infection; and culturing the helper cells under conditions to produce recombinant viral (e.g., AAV) particles. In another embodiment, a method of producing recombinant viral or AAV particles with reduced amounts of recombinant viral (e.g., AAV) particles in which the recombinant viral vector includes contaminating nucleic acid, includes introducing into a packaging helper cell a recombinant vector (e.g., AAV) plasmid; and culturing the helper cells under conditions to produce recombinant viral (e.g., AAV) particles, wherein the recombinant viral (e.g., AAV) particles produced have reduced numbers of viral (e.g., AAV) particles with recombinant vector genomes that contain contaminating nucleic acid compared to the numbers of viral (e.g., AAV) particles that contain contaminating nucleic acid produced under conditions in which the filler or stuffer polynucleotide sequence is absent from the recombinant viral vector. In particular aspects, the contaminating nucleic acid is bacterial nucleic acid; or a sequences other than the heterologous polynucleotide sequence, or ITR, promoter, enhancer, origin of replication, poly-Adenine sequence, or selectable marker.

Helper cells include mammalian cells. Helper cells also include insect cells, such as F9 cells. In particular embodiments, a helper cell provides helper (e.g., AAV) functions to package the heterologous polynucleotide sequence into a viral particle. In particular aspects, a helper cell provides AAV Rep and/or Cap proteins (e.g., Rep78 or/and Rep68 proteins); a helper cell is stably or transiently transfected with polynucleotide(s) encoding Rep and/or Cap protein sequence(s); a helper cell is stably or transiently transfected with Rep78 and/or Rep68 protein polynucleotide encoding sequence(s).

Invention recombinant vector (e.g., AAV) plasmids can be based upon any strain or serotype, including hybrids or chimeras of different serotypes. Invention recombinant viral (e.g., AAV) particles can also be based upon any strain or serotype, including hybrids or chimeras of different serotypes. Representative AAV serotypes include, without limitation, AAV1, AAV2, AAV3, AAV4, AAV5, AAV6, AAV7, AAV8, AAV9, AAV10, AAV11, Rh74, and Rh10 serotypes. Furthermore, invention recombinant vector (e.g., AAV) plasmids can include elements from any one serotype, a mixture of serotypes, or hybrids or chimeras of different serotypes. In various embodiments, an recombinant AAV vector plasmid includes a Cap, Rep, and/or ITR sequence derived from AAV1, AAV2, AAV3, AAV4, AAV5, AAV6, AAV7, AAV8, AAV9, AAV10, AAV11, Rh74, or Rh10 serotype, or a hybrid or chimera of any of the foregoing AAV serotypes. Moreover, invention recombinant viral (e.g., AAV) particles comprising vector genomes can include one or more capsid proteins from any one serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, Rh74, Rh10 serotype.

DESCRIPTION OF DRAWINGS

FIG. 1 shows levels of plasmid DNA impurities in purified AAV vector preparations depend on the size of the transgene cassette.

FIG. 2 shows mapping of the 5 end of the vector genome using PCR and a set of primers spanning transgene cassette and upstream plasmid backbone sequences in vector preparation before and after treatment with DNase 1. A single primer located in the transgene cassette (circle) was used in combination with primers spanning sequence in transgene cassette and flanking segment of plasmid backbone containing antibiotic resistance (KanR and AmpR) gene. PCR reactions were analyzed by 1% agarose gel electrophoresis.

FIGS. 2A-2D show PCR on Vector with Short and Long Transgene Cassettes before and after DNase treatment. A) shows PCR on Vector with Short Transgene cassette (2.7 kb) before DNase treatment; B) shows PCR on Vector with Short Transgene cassette (2.7 kb) after DNase treatment and DNA purification; C) shows PCR on Vector with Long Transgene Cassette (4.3 kb) before DNase treatment; and D) shows PCR on Vector with Long transgene cassette (4.2 kb) after DNase treatment and DNA purification.

FIGS. 3A-3B show plasmid controls PCR was performed on the production plasmid DNA bearing the transgene cassette using same set of primers before and after treatment with DNase 1. A) shows plasmid with Transgene cassette (2.7 kb); B) shows plasmid with Transgene cassette (4.3 kb); and C) shows after DNase treatment of plasmid samples with DNase.

FIG. 4 is a diagram showing encapsidation of plasmid DNA in vectors with short transgene cassette.

FIG. 5 shows that an oversized plasmid backbone in trans (7.1 Kb) exceeding the AAV packaging limit markedly reduces non-vector DNA packaging.

FIG. 6 shows residual plasmid DNA in purified AAV vectors made with vector plasmids containing non oversized (circles) versus oversized (triangles) backbones.

FIG. 7 shows Vector Generation in HEK293 cell culture and vector purification (downstream).

DETAILED DESCRIPTION

The studies disclosed herein show that levels of residual plasmid DNA impurities were elevated in recombinant adeno-associated virus (rAAV) vector plasmids with vector expression cassettes shorter than the natural rAAV packaging limit (approximately 4.7 kb), and that the shorter the sequences than the natural rAAV packaging limit the greater the level of impurities. In particular for example, rAAV A (2.7 kb size) contained 164 pg/$10^9$ vg (n=9) residual plasmid DNA; rAAV B (3.7 kb size) contained 42.7 pg/$10^9$ vg (n 32); and rAAV C (4.3 kb size) contained 14.0 pg/$10^9$ vg (n 29). Accordingly, the studies demonstrate that adjusting the length of expression cassette during vector design so length is at or close to the (natural) packaging limit of viral (AAV) capsid will reduce or prevent encapsidation of contaminating nucleic acid, which in turn reduces viral (AAV) particles with encapsidated nucleic acid impurities.

The invention therefore provides recombinant vector (e.g., AAV) plasmids with a sequence having a size approaching the natural packaging capacity of the virus (AAV), and methods of using such recombinant vector (e.g., AAV) plasmids, for example, to produce recombinant virus particles having reduced or eliminated residual DNA impurities. For example, optimizing the size of the vector genome sequence will mitigate the potential risks associated with vector mediated transfer of undesirable nucleic acid sequences, such as bacterial genes causing antibiotic resistance.

Invention recombinant vector (e.g., AAV) plasmids in which the packaged (encapsidated) portion (referred to as the "vector" or "vector genome") has a size approaching the natural packaging capacity of the virus (e.g., AAV) can be used to transfer/deliver heterologous polynucleotide sequences, such as coding sequences (genes) for proteins that provide a desirable or therapeutic benefit, as well as inhibitory (e.g., anti-sense) nucleic acid that reduce or inhibit expression of an undesirable or defective (e.g., pathologic) gene, thereby treating a variety of diseases. For example, a recombinant vector (e.g., AAV) plasmid in which the packaged (encapsidated) portion (vector genome) has a size approaching the natural packaging capacity of the virus (AAV) can be used to transfer/deliver therapeutic genes to treat a genetic deficiency disease, such as hemophilia A, B; other metabolic or plasma protein deficiencies; and for other therapeutic purposes.

As set forth herein, recombinant vector (e.g., AAV) plasmids can be used to deliver polynucleotide sequences (e.g., heterologous polynucleotide sequences) to cells ex vivo, in vitro and in vivo. Such polynucleotide sequences can encode proteins such that the cells into which the polynucleotides are delivered express the encoded proteins. For example, a recombinant vector (e.g., AAV) plasmid can include a heterologous polynucleotide sequence encoding a desired (e.g., therapeutic) protein or peptide. In addition, a recombinant vector (e.g., AAV) plasmid can include a heterologous polynucleotide sequence that when transcribed comprises an inhibitory sequence (e.g., RNA), for example, a sequence that targets a gene (or gene transcript) for inhibition of expression. Vector delivery or administration to a subject (e.g., mammal) therefore provides not only polynucleotides encoding proteins and peptides to the subject, but also inhibitory nucleic acids that target genes for inhibition of expression or function in the subject.

Thus, in accordance with the invention recombinant vector (e.g., AAV) plasmids where the packaged (encapsidated) portion (vector genome) has a size approaching the natural packaging capacity of the virus (e.g., AAV), including heterologous polynucleotide sequences encoding peptides and proteins, as well as heterologous polynucleotide sequences which directly or when transcribed comprise inhibitory nucleic acids that target genes for inhibition of expression or function, are provided. In addition, such vector genomes can be included (packaged) within a virus, such as an adeno-associated virus (e.g., AAV). Thus, a recombinant vector (e.g., AAV) plasmid where the vector genome has a size approaching the natural packaging capacity of the virus can be packaged into a virus (also referred to herein as a "particle" or "virion") for subsequent infection (transformation) of a cell, ex vivo, in vitro or in vivo.

Such particles or virions will typically include proteins that encapsidate or package the vector genome. Particular examples include viral envelope proteins, and in the case of AAV, capsid proteins.

A recombinant "vector plasmid" or "AAV vector plasmid" is derived from the wild type genome of a virus, such as AAV by using molecular methods to remove the wild type genome from the virus (e.g., AAV), and replacing with a non-native nucleic acid, such as a heterologous polynucleotide sequence (e.g., a therapeutic gene expression cassette). Typically, for AAV one or both inverted terminal repeat (ITR) sequences of the wild type AAV genome are retained in the AAV vector plasmid. A viral vector (e.g., AAV) is distinguished from a viral (e.g., AAV) genome, since all or a part of the viral genome has been replaced with a heterologous polynucleotide sequence, which heterologous polynucleotide sequence is typically a non-native nucleic acid with respect to the viral (e.g., AAV) genomic nucleic acid.

Incorporation of a heterologous polynucleotide therefore defines the viral vector (e.g., AAV) as a "recombinant" vector, which in the case of AAV can be referred to as an "rAAV vector." Where a recombinant vector genome is encapsidated or packaged into an AAV particle, the particle can be referred to as a "rAAV."

In particular embodiments, a recombinant vector (e.g., AAV) plasmid is a parvovirus vector. Parvoviruses are small viruses with a single-stranded DNA genome. "Adeno-associated viruses" (AAV) are in the parvovirus family.

Parvoviruses including AAV are viruses useful as gene therapy vectors as they can penetrate cells and introduce nucleic acid/genetic material. These viruses are useful as gene therapy vectors as they can penetrate cells and introduce nucleic acid/genetic material so that the nucleic acid/genetic material is stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous polynucleotide sequences (e.g., therapeutic proteins and agents) to human patients without causing substantial AAV pathogenesis or disease.

Such vector plasmids (e.g., AAV), and particles (e.g., AAV) including such vector genomes, include any virus strain or serotype, and subgroups and variants thereof. As used herein, the term "serotype" is a distinction used to refer to a virus (e.g., AAV) having a capsid that is serologically distinct from other virus (e.g., AAV) serotypes. A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

By way of a non-limiting example, AAV include various naturally and non-naturally occurring serotypes. Such non-limiting serotypes include, for example, AAV-1, -2, -3, -4, -5, -6, -7, -8, -9, -10, -11, -rh74, -rh10 and AAV-2i8. Again, for the sake of convenience serotypes include AAV with capsid sequence modifications that have not been fully characterized as being a distinct serotype, and may in fact actually constitute a subgroup or variant of a known serotype.

Accordingly, invention recombinant vector (e.g., AAV) plasmids, and particles that include packaged or encapsidated vector genomes, as well as methods and uses thereof, include any viral strain or serotype. As a non-limiting example, a recombinant vector (e.g., AAV) plasmid can be based upon any AAV genome, such as AAV-1, -2, -3, -4, -5, -6, -7, -8, -9, -10, -11, -rh74, -rh10 or AAV-2i8, for example. A particle (virus) that packages (also referred to as encapsidates) a recombinant vector (e.g., AAV) genome can be based upon any AAV serotype such as AAV-1, -2, -3, -4, -5, -6, -7, -8, -9, -10, -11, -rh74, -rh10 or AAV-2i8, for example. Such vectors and particles can be based on the same of strain or serotype (or subgroup or variant), or be different from each other. As a non-limiting example, a recombinant vector (e.g., AAV) plasmid can be based upon AAV2 serotype genome can be identical to one or more of the capsid proteins that package the vector, in which case at least one of the three capsid proteins would also be AAV2. In addition, a recombinant vector (e.g., AAV) plasmid can be based upon AAV2 serotype genome can be distinct serotype from one or more of the capsid proteins that package the vector, in which case at least one of the three capsid proteins could be a non-AAV2 capsid, such as AAV-1, -3, -4, -5, -6, -7, -8, -9, -10, -11, -rh74, -rh10 or AAV-2i8 capsid, for example.

Furthermore, a recombinant vector (e.g., AAV) plasmid, and particles that can include the packaged (encapsidated) portion (vector genome) include hybrids or chimeras. Thus, as a non-limiting example, a hybrid vector genome can be one virus genome serotype, such as an AAV2 serotype and a non-AAV2 serotype, for example, an AAV2 flanking (5' or 3') ITR, and a non-AAV2 flanking (5' or 3') ITR. More particularly, as non-limiting example, a vector genome that is hybrid AAV serotype, could be an AAV2 flanking (5' or 3') ITR and an AAV-1, -3, -4, -5, -6, -7, -8, -9, -10, -11, -rh74, -rh10 or AAV-2i8 flanking (5' or 3') ITR. As another non-limiting example, a virus can be a hybrid AAV serotype, such as an AAV2 capsid and a non-AAV2 capsid, for example, an AAV2 VP1, VP2 or VP3, and a non-AAV2 VP1, VP2 or VP3. More particularly, a hybrid or chimeric virus that is an AAV serotype, could be an AAV2 VP1, VP2 or VP3 and a AAV-1, -3, -4, -5, -6, -7, -8, -9, -10, -11, -rh74, -rh10 or AAV-2i8 VP1, VP2 or VP3.

Recombinant vector (e.g., AAV) plasmids (e.g., AAV includes one or more AAV ITRs) and particles (e.g., that include AAV capsid proteins) as set forth herein include those having a polynucleotide, polypeptide or subsequence thereof that has less than 100% sequence identity to a reference sequence. In various embodiments, a sequence that has less than 100% sequence identity to a reference sequence is at least 80% or more (e.g., 80-85%, 85-90%, 90-95%, 96%, 97%, 98%, 99%, 99.5%, etc.) identical to a reference sequence, for example, 80% or more (e.g., 80-85%, 85-90%, 90-95%, 96%, 97%, 98%, 99%, 99.5%, etc.) identical to any of AAV1, AAV2, AAV3, AAV4, AAV5, AAV6, AAV7, AAV8, AAV9, AAV10, AAV11, Rh10, Rh74 5' or 3' ITR or AAV-2i8 VP1, VP2, and/or VP3 capsid sequence. Such 5' and 3' ITR and capsid sequences for AAV1, AAV2, AAV3, AAV4, AAV5, AAV6, AAV7, AAV8, AAV9, AAV10, AAV11, Rh10, Rh74 and AAV-2i8 are known in the art.

Recombinant vector (e.g., AAV) plasmids, including AAV1, AAV2, AAV3, AAV4, AAV5, AAV6, AAV7, AAV8, AAV9, AAV10, AAV11, Rh10, Rh74 or AAV-2i8 and related, hybrid and chimeric sequences, can be constructed using recombinant techniques that are known to the skilled artisan, to include one or more heterologous polynucleotide sequences (transgenes) flanked with one or more functional AAV ITR sequences.

Such vector plasmids can have one or more of the wild type AAV genes deleted in whole or in part, for example, a rep and/or cap gene, but retain at least one functional flanking ITR sequence, as necessary for the rescue, replication, and packaging of the AAV vector particle. Thus, an AAV vector genome includes sequences required in cis for replication and packaging (e.g., functional ITR sequences).

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally altered or modified polynucleotides as well as analogues and derivatives. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "heterologous" polynucleotide refers to a polynucleotide inserted into a vector (e.g., AAV) plasmid for purposes of vector (e.g., AAV) mediated transfer/delivery of the polynucleotide into a cell. Heterologous polynucleotides are typically distinct from viral (e.g., AAV) nucleic acid, i.e., are "non-native" with respect to viral (e.g., AAV) nucleic acid. Once transferred/delivered into the cell, a heterologous polynucleotide, contained within the virion (e.g., AAV), can be expressed (e.g., transcribed, and translated if appropriate). Alternatively, a transferred/delivered heterologous polynucleotide in a cell, contained within the virion, need not be expressed. Although the term "heterologous" is not always used herein in reference to polynucleotides, reference to a polynucleotide even in the absence of the modifier "heterologous" is intended to include heterologous polynucleotides in spite of the omission.

The "polypeptides," "proteins" and "peptides" encoded by the "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the polynucleotide sequences can be but are not required to be identical to the endogenous protein that is defective, or whose expression is insufficient, or deficient in the treated mammal.

Invention recombinant vector (e.g., AAV) plasmids can be used to introduce/deliver polynucleotides stably or transiently into cells and progeny thereof. The term "transgene" is used herein to conveniently refer to a heterologous polynucleotide that has been introduced into a cell or organism. Transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription).

For example, in a cell having a transgene, the transgene has been introduced/transferred by way of vector (e.g., AAV) "transformation" or "transfection" of the cell. The terms "transform," and "transfect" refer to introduction of a molecule such as a polynucleotide into a cell or host organism. A cell into which the transgene has been introduced is referred to as a "transformed cell" or "transformant." Accordingly, a "transformed" or "transfected" cell (e.g., in a mammal, such as a cell or tissue or organ cell), means a genetic change in a cell following incorporation of an exogenous molecule, for example, a polynucleotide or protein (e.g., a transgene) into the cell. Thus, a "transfected" or "transformed" cell is a cell into which, or a progeny thereof in which an exogenous molecule has been introduced, for example. The cell(s) can be propagated and the introduced protein expressed, or nucleic acid transcribed. For gene therapy uses and methods, a transformed cell can be in a subject.

The introduced polynucleotide may or may not be integrated into nucleic acid of the recipient cell or organism. If an introduced polynucleotide becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism only transiently.

Cells that may be transformed include a cell of any tissue or organ type, of any origin (e.g., mesoderm, ectoderm or endoderm). Non-limiting examples of cells include liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (e.g., retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells. Additional examples include stem cells, such as pluripotent or multipotent progenitor cells that develop or differentiate into liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (retinal, cell components) spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

A "therapeutic molecule" in one embodiment is a peptide or protein that may alleviate or reduce symptoms that result from an absence or defect in a protein in a cell or subject. Alternatively, a "therapeutic" peptide or protein encoded by a transgene is one that confers a benefit to a subject, e.g., to correct a genetic defect, to correct a gene (expression or functional) deficiency, or an anti-cancer effect.

Particular non-limiting examples of heterologous polynucleotides encoding gene products (e.g., therapeutic proteins) which are useful in accordance with the invention include, but are not limited to: genes that comprise or encode CFTR (cystic fibrosis transmembrane regulator protein), a blood coagulation (clotting) factor (Factor XIII, Factor IX, Factor X, Factor VIII, Factor VIIa, protein C etc.) including gain of function blood coagulation factors, an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, 0-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes [de Groot et al., Blood 2008 Oct. 15; 112(8):3303], or hCDR1 [Sharabi et al., Proc Natl Acad Sci USA. 2006 Jun. 6; 103(23):8810-5], insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

Further non-limiting examples of heterologous polynucleotides encoding gene products (e.g., therapeutic proteins) which are useful in accordance with the invention include those that may be used in the treatment of a disease or disorder including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

All mammalian and non-mammalian forms of polynucleotides encoding gene products, including the non-limiting genes and proteins disclosed herein are expressly included, either known or unknown. Thus, the invention includes genes and proteins from non-mammals, mammals other than humans, and humans, which genes and proteins function in a substantially similar manner to the human genes and proteins described herein. A non-limiting example of non-mammalian gene is a Fok nuclease domain, which is bacterial in origin. Non-limiting examples of mammalian non-human FIX sequences are described in Yoshitake et al., 1985, supra; Kurachi et al., 1995, supra; Jallat et al., 1990, supra; Kurachi et al., 1982, Proc. Natl. Acad. Sci. USA 79:6461-6464; Jaye et al., 1983, Nucl. Acids Res. 11:2325-2335; Anson et al., 1984, EMBO J. 3: 1053-1060; Wu et al., 1990, Gene 86:275-278; Evans et al., Proc Natl Acad Sci USA 86:10095 (1989), Blood 74:207-212; Pendurthi et al., 1992, Thromb. Res. 65:177-186; Sakar et al., 1990, Genomics 1990, 6:133-143; and, Katayama et al., 1979, Proc. Natl. Acad. Sci. USA 76:4990-4994.

As set forth herein, heterologous polynucleotide sequences (transgenes) include inhibitory and antisense nucleic acid sequences. Inhibitory, antisense, siRNA, miRNA, shRNA, RNAi and antisense oligonucleotides can modulate expression of a target gene. Such molecules include those able to inhibit expression of a target gene involved in mediation of a disease process, thereby reducing, inhibiting or alleviating one or more symptoms of a disease.

Antisense includes single, double or triple stranded polynucleotides and peptide nucleic acids (PNAs) that bind RNA transcript or DNA (e.g., genomic DNA). Oligonucleotides derived from the transcription initiation site of a target gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., Cell 95:1017 (1998); and Fire et al., Nature, 391:806 (1998)). Double stranded RNA sequences from a target gene coding region may therefore be used to inhibit or prevent gene expression/transcription in accordance with the methods and uses of the invention. Antisense and RNAi can be produced based upon nucleic acids encoding target gene sequences (e.g., huntingtin, or HTT), such as nucleic acid encoding mammalian and human HTT. For example, a single or double stranded nucleic acid (e.g., RNA) can target HTT transcript (e.g., mRNA).

A "siRNA" refers to a therapeutic molecule involved in the RNA interference process for a sequence-specific post-transcriptional gene silencing or gene knockdown. siRNAs have homology with the sequence of the cognate mRNA of the targeted gene. Small interfering RNAs (siRNAs) can be synthesized in vitro or generated by ribonuclease III cleavage from longer dsRNA and are the mediators of sequence-specific mRNA degradation. siRNA or other such nucleic acids of the invention can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting mRNA of a target gene may be between 15-50 nucleotides in length, and more typically about 20-30 nucleotides in length. Such nucleic acid molecules can be readily incorporated into the viral vectors disclosed herein using conventional methods known to one of skill in the art.

Particular non-limiting examples of genes (e.g., genomic DNA) or transcript of a pathogenic gene (e.g., RNA or mRNA) that may be targeted with inhibitory nucleic acid sequences in accordance with the invention include, but are not limited to: genes associated with polynucleotide repeat diseases such as huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular edema (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; or mutant rhodopsin gene (RHO) in autosomal dominantly inherited retinitis pigmentosa (adRP).

Polynucleotides, polypeptides and subsequences thereof include modified and variant forms. As used herein, the terms "modify" or "variant" and grammatical variations thereof, mean that a polynucleotide, polypeptide or subsequence thereof deviates from a reference sequence. Modified and variant sequences may therefore have substantially the same, greater or less activity or function than a reference sequence, but at least retain partial activity or function of the reference sequence.

Accordingly, the invention also includes naturally and non-naturally occurring variants. Such variants include gain and loss of function variants. For example, wild type human FIX DNA sequences, which protein variants or mutants retain activity, or are therapeutically effective, or are comparably or even more therapeutically active than invariant human FIX in the methods and uses of the invention. In a particular example, collagen IV serves to trap FIX, meaning that when introduced into the muscle tissue of a mammal some of the FIX is not available for participation in blood coagulation because it is retained in the interstitial spaces in the muscle tissue. A mutation in the sequence of FIX that results in a protein with reduced binding to collagen IV (e.g., loss of function) is a mutant useful in the methods of the invention, for example, for treatment of hemophilia. An example of such a mutant human FIX gene encodes a human FIX protein with the amino acid alanine in place of lysine in the fifth amino acid position from the beginning of the mature protein.

Non-limiting examples of modifications include one or more nucleotide or amino acid substitutions (e.g., 1-3, 3-5, 5-10, 10-15, 15-20, 20-25, 25-30, 30-40, 40-50, 50-100, or more nucleotides or residues), additions (e.g., insertions or 1-3, 3-5, 5-10, 10-15, 15-20, 20-25, 25-30, 30-40, 40-50, 50-100, or more nucleotides or residues) and deletions (e.g., subsequences or fragments) of a reference sequence. In particular embodiments, a modified or variant sequence retains at least part of a function or an activity of unmodified sequence. Such modified forms and variants can have less than, the same, or greater, but at least a part of, a function or activity of a reference sequence, for example, as described herein.

A variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

Accordingly, the invention includes gene and protein variants (e.g., of polynucleotides encoding proteins described herein) which retain one or more biological activities (e.g., function in blood clotting, etc.). Such variants of proteins or polypeptides include proteins or polypeptides which have been or may be modified using recombinant DNA technology such that the protein or polypeptide possesses altered or additional properties, for example, variants conferring enhanced protein stability in plasma or enhanced activity of the protein. Variants can differ from a reference sequence, such as naturally occurring polynucleotides, proteins or peptides.

At the nucleotide sequence level, a naturally and non-naturally occurring variant gene will typically be at least about 50% identical, more typically about 70% identical, even more typically about 80% identical (90% or more identity) to the reference gene. At the amino acid sequence level, a naturally and non-naturally occurring variant protein will typically be at least about 70% identical, more typically about 80% identical, even more typically about 90% or more identity to the reference protein, although substantial regions of non-identity are permitted in non-conserved regions (e.g., less, than 70% identical, such as less than 60%, 50% or even 40%). In other embodiments, the sequences have at least 60%, 70%, 75% or more identity (e.g., 80%, 85% 90%, 95%, 96%, 97%, 98%, 99% or more identity) to a reference sequence. Procedures for the introduction of nucleotide and amino acid changes in a polynucleotide, protein or polypeptide are known to the skilled artisan (see, e.g., Sambrook et al., *Molecular Cloning: A Laboratory Manual* (2007)).

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence.

The identity can extend over the entire sequence length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous amino acids. In additional particular aspects, the length of the sequence sharing identity is 20 or more contiguous polynucleotide or amino acids, e.g., 20, 21, 22, 23, 24, 25, 26, 27, 28, 29, 30, 31, 32, 33, 34, 35, etc. contiguous amino acids. In further particular aspects, the length of the sequence sharing identity is 35 or more contiguous polynucleotide or amino acids, e.g., 35, 36, 37, 38, 39, 40, 41, 42, 43, 44, 45, 45, 47, 48, 49, 50, etc., contiguous amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 95-100, 100-110, etc. contiguous polynucleotide or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Polynucleotides include additions and insertions, for example, heterologous domains. An addition (e.g., heterologous domain) can be a covalent or non-covalent attachment of any type of molecule to a composition. Typically additions and insertions (e.g., a heterologous domain) confer a complementary or a distinct function or activity.

Additions and insertions include chimeric and fusion sequences, which is a polynucleotide or protein sequence having one or more molecules not normally present in a reference native (wild type) sequence covalently attached to the sequence. The terms "fusion" or "chimeric" and grammatical variations thereof, when used in reference to a molecule means that a portions or part of the molecule contains a different entity distinct (heterologous) from the molecule as they do not typically exist together in nature. That is, for example, one portion of the fusion or chimera, includes or consists of a portion that does not exist together in nature, and is structurally distinct.

The term "vector" refers to a plasmid, virus (e.g., AAV vector), cosmid, or other vehicle that can be manipulated by insertion or incorporation of a polynucleotide. Such vectors can be used for genetic manipulation (i.e., "cloning vectors"), to introduce/transfer polynucleotides into cells, and to transcribe or translate the inserted polynucleotide in cells. A vector plasmid generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

As used herein, the term "recombinant," as a modifier of a viral vector such as AAV vector, as well as a modifier of sequences such as recombinant polynucleotides and polypeptides, means that the compositions have been manipulated (i.e., engineered) in a fashion that generally does not occur in nature. A particular example of a recombinant vector, such as AAV vector would be where a polynucleotide that is not normally present in the wild-type viral (e.g., AAV) genome is within the viral (e.g., AAV) particle and/or viral (e.g., AAV) genome. For example, a particular example of a recombinant polynucleotide would be where a polynucleotide (e.g., gene) encoding a protein is cloned into a vector, with or without 5', 3' and/or intron regions that the gene is normally associated within the viral (e.g., AAV) genome. Although the term "recombinant" is not always used herein in reference to viral vectors such as AAV vectors, as well as sequences such as polynucleotides and polypeptides, hybrids and chimeras, recombinant forms of (e.g., AAV), vectors, and sequences including polynucleotides and polypeptides, hybrids and chimeras, are expressly included in spite of any such omission.

For a recombinant vector plasmid, a vector genome refers to the portion of the vector plasmid that is packaged or encapsidated by virus (e.g., AAV), which contains the heterologous polynucleotide sequence. The plasmid portion of the recombinant vector plasmid includes the backbone used for helper cell transfection and cell production of virus that packages/encapsidates the vector genome, but is not itself packaged or encapsidated by virus (e.g., AAV).

A viral vector is derived from or based upon one or more nucleic acid elements that comprise a viral genome. Particular viral vectors include parvovirus vectors, such as adeno-associated virus (AAV) vectors.

Recombinant vector plasmids as set forth herein include an additional filler/stuffer nucleic acid sequence that resizes or adjusts the length to near or at the normal size of the virus genomic sequence that is packaged or encapsidated to form infectious virus particles. In various embodiments, a filler/stuffer nucleic acid sequence is an untranslated (non-protein encoding) segment of nucleic acid. In particular embodiments of an AAV vector, a heterologous polynucleotide sequence has a length less than 4.7 Kb and the filler or stuffer polynucleotide sequence has a length that when combined (e.g., inserted into a vector) with the heterologous polynucleotide sequence has a total length between about 3.0-5.5 Kb, or between about 4.0-5.0 Kb, or between about 4.3-4.8 Kb. For example, length of a vector for AAV particle packaging can be up to about 5.2 kb. More particularly, a filler or stuffer polynucleotide sequence has a sequence length between 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000 nucleotides in length.

As disclosed herein, the filler or stuffer polynucleotide sequence can be in any position within the recombinant vector plasmid, relative to other sequences, such as the heterologous polynucleotide sequence, control element(s), ITR(s), origin of replication, selectable marker, etc., compatible with vector function. In a particular aspect, a filler or stuffer polynucleotide sequence is positioned between a 5' and 3' ITR that flanks the respective 5' or 3' termini of the heterologous polynucleotide sequence, e.g., in the context of AAV vector plasmid the filler or stuffer polynucleotide sequence is present in the vector genome portion of the recombinant vector plasmid and is therefore available for virus packaging/encapsidation. In another particular aspect, a filler or stuffer polynucleotide sequence is positioned outside a 5' and 3' ITR that flanks the respective 5' or 3' termini of the heterologous polynucleotide sequence, e.g., in the context of AAV vector plasmid the filler or stuffer polynucleotide sequence is present in the backbone or plasmid portion of the recombinant vector plasmid. In a further particular aspect, a filler or stuffer polynucleotide sequence is positioned within the heterologous polynucleotide sequence, e.g., in the context of AAV vector plasmid the filler or stuffer polynucleotide sequence positioned within the heterologous polynucleotide sequence is present in the vector genome portion of the recombinant vector plasmid and is therefore available for virus packaging/encapsidation.

Recombinant vector plasmids including recombinant AAV vector plasmids of the invention can include still additional nucleic acid elements. These elements include, without limitation one or more copies of an AAV ITR sequence, a promoter or enhancer element, a transcription termination signal, 5' or 3' untranslated regions (e.g., polyadenylation sequences) which flank a polynucleotide sequence, or all or a portion of intron I. Such elements also optionally include a transcription termination signal. A particular non-limiting example of a transcription termination signal is the SV40 transcription termination signal.

Recombinant vector plasmids of the invention can include one or more "expression control elements." Control elements, including expression control elements as set forth herein, present within a vector facilitate proper heterologous polynucleotide transcription and if appropriate translation (e.g., splicing signal for introns, maintenance of the correct reading frame of the gene to permit in-frame translation of mRNA and, stop codons etc.). Typically, expression control elements are nucleic acid sequence(s), such as promoters and enhancers that influence expression of an operably linked heterologous polynucleotide. Such elements typically act in cis but may also act in trans.

Expression control can be effected at the level of transcription, translation, splicing, message stability, etc. Typically, an expression control element that modulates transcription is juxtaposed near the 5' end of the transcribed polynucleotide (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, 5000 to 10,000 or more nucleotides from the polynucleotide), even at considerable distances. Nevertheless, owing to the polynucleotide length limitations for viral vectors, such as AAV vectors, such expression control elements will typically be within 1 to 1000 nucleotides from the polynucleotide.

Functionally, expression of operably linked heterologous polynucleotide is at least in part controllable by the element (e.g., promoter) such that the element modulates transcription of the heterologous polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

The term "promoter" as used herein can refer to a DNA sequence that is located adjacent to a polynucleotide sequence that encodes a recombinant product. A promoter is typically operatively linked to an adjacent sequence, e.g., heterologous polynucleotide. A promoter typically increases an amount expressed from a heterologous polynucleotide as compared to an amount expressed when no promoter exists.

The term "enhancer" as used herein can refer to a sequence that is located adjacent to the heterologous polynucleotide. Enhancer elements are typically located upstream of a promoter element but also function and can be located downstream of or within a DNA sequence (e.g., a heterologous polynucleotide). Hence, an enhancer element can be located 100 base pairs, 200 base pairs, or 300 or more base pairs upstream or downstream of a heterologous polynucleotide. Enhancer elements typically increase expressed of a heterologous polynucleotide above increased expression afforded by a promoter element.

Expression control elements (e.g., promoters) include those active in a particular tissue or cell type, referred to herein as a "tissue-specific expression control elements/promoters." Tissue-specific expression control elements are typically active in specific cell or tissue (e.g., active in a liver, brain, central nervous system, spinal cord, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type.

For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li, et al., *Nat. Biotech.* 17:241-245 (1999). Examples of promoters that are tissue-specific for liver are albumin, Miyatake, et al. *J. Virol.,* 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.,* 7:1503-14 (1996)], bone (osteocalcin, Stein, et al., *Mol. Biol. Rep.,* 24:185-96 (1997); bone sialoprotein, Chen, et al., *J. Bone Miner. Res.* 11:654-64 (1996)), lymphocytes (CD2, Hansal, et al., *J. Immunol.,* 161:1063-8 (1998); immunoglobulin heavy chain; T cell receptor a chain), neuronal (neuron-specific enolase (NSE) promoter, Andersen, et al., *Cell. Mol. Neurobiol.,* 13:503-15 (1993); neurofilament light-chain gene, Piccioli, et al., *Proc. Natl. Acad. Sci.* USA, 88:5611-5 (1991); the neuron-specific vgf gene, Piccioli, et al., *Neuron,* 15:373-84 (1995)]; among others.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the heterologous polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of operably linked heterologous polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci.* USA, 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin. Invest.* 100:2865-2872 (1997); Rivera, et al., *Nat. Medicine.* 2:1028-1032 (1996)). Other types of regulatable control elements which may be useful in this context are those which are regulated by a specific physiological state, e.g., temperature, acute phase.

Expression control elements also include the native elements(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

As disclosed herein, AAV vectors typically accept inserts of DNA having a defined size range which is generally about 4 kb to about 5.2 kb, or slightly more. Thus, for shorter sequences, inclusion of the stuffer or filler in the insert fragment in order to achieve the length acceptable for AAV vector packaging into virus particle. As also disclosed herein, an intron can also function as a filler or stuffer polynucleotide sequence in order to achieve a length for AAV vector packaging into a virus particle. Introns and intron fragments (e.g. portion of intron I of FIX) that function as a filler or stuffer polynucleotide sequence also can enhance expression. For example, inclusion of an intron element may enhance expression compared with expression in the absence of the intron element (Kurachi et al., 1995, supra).

The use of introns is not limited to the inclusion of FIX intron I sequences, but also include other introns, which introns may be associated with the same gene (e.g., where the heterologous polynucleotide encodes FIX, the intron is derived from an intron present in the FIX genomic sequence) or a completely different gene or other DNA sequence. Accordingly, other untranslated (non-protein encoding) regions of nucleic acid, such as introns found in genomic sequences from cognate (related) genes (the heterologous polynucleotide sequence encodes all or a portion of same protein encoded by the genomic sequence) and non-cognate (unrelated) genes (the heterologous polynucleotide sequence encodes a protein that is distinct from the protein encoded by the genomic sequence) can also function as filler or stuffer polynucleotide sequences in accordance with the invention.

A "portion of intron I" as used herein, is meant region of intron I having a nucleotide length of from about 0.1 kb to about 1.7 kb, which region enhances expression of FIX, typically by about 1.5-fold or more on a plasmid or viral vector template when compared with expression of FIX in the absence of a portion of intron I. A more specific portion is a 1.3 kb portion of intron 1.

The term "oligonucleotide" as used herein refers to sequences, primers and probes defined as a nucleic acid molecule comprised of two or more ribo- or deoxyribonucleotides, typically more than three. The exact size of the oligonucleotide will depend on various factors and on the particular application and use of the oligonucleotide, but typically an oligonucleotide has a length between about 5-50 nucleotides.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-30 or more nucleotides in length. The primer must be of sufficient complementarity to the desired template to prime the synthesis of the desired extension product, that is, to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188.

The phrase "specifically hybridize" refers to the association between two single-stranded nucleic acid molecules of sufficiently complementary sequence to permit hybridization under pre-determined conditions generally used in the art (sometimes termed "substantially complementary"). In particular, the term refers to hybridization of two polynucleotide sequences with substantially complementary sequences, to the substantial exclusion of hybridization with other single-stranded non-complementary nucleic acid sequences.

Polynucleotides and polypeptides including modified forms can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

A "selectable marker gene" refers to a gene that when expressed confers a selectable phenotype, such as antibiotic resistance (e.g., kanamycin), on a transformed cell. A "reporter" gene is one that provides a detectable signal. A non-limiting example of a reporter gene is the luciferase gene.

As used herein, the term "operable linkage" or "operably linked" refers to a physical or functional juxtaposition of the components so described as to permit them to function in their intended manner. In the example of an expression control element in operable linkage with a heterologous polynucleotide, the relationship is such that the control element modulates expression of the heterologous polynucleotide. More specifically, for example, two DNA sequences operably linked means that the two DNAs are arranged (cis or trans) in such a relationship that at least one of the DNA sequences is able to exert a physiological effect upon the other sequence.

Polynucleotides and polypeptides including modified forms can also be produced by chemical synthesis using methods known to the skilled artisan, for example, an automated synthesis apparatus (see, e.g., Applied Biosystems, Foster City, Calif.). Peptides can be synthesized, whole or in part, using chemical methods (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid phase techniques (see, e.g., Roberge *Science* 269:202 (1995); Merrifield, *Methods Enzymol.* 289:3(1997)) and automated synthesis may be achieved, e.g., using the ABI 431A Peptide Synthesizer (Perkin Elmer) in accordance with the manufacturer's instructions.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude combinations produced by the hand of man, for example, a recombinant vector (e.g., AAV) plasmid, or virus particle that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

Methods and uses of the invention provide a means for delivering (transducing) heterologous polynucleotides (transgenes) into a broad range of host cells, including both dividing and non-dividing cells. The recombinant vector (e.g., AAV) plasmids, vector genomes, recombinant virus particles, methods, uses and pharmaceutical formulations of the invention are additionally useful in a method of administering a protein, peptide or nucleic acid to a subject in need thereof, as a method of treatment. In this manner, the protein, peptide or nucleic acid may thus be produced in vivo in a subject. The subject may benefit from or be in need of the protein, peptide or nucleic acid because the subject has a deficiency of the protein, peptide or nucleic acid, or because the production of the protein, peptide or nucleic acid in the subject may impart some therapeutic effect, as a method of treatment or otherwise. Alternatively, it may be desirable to inhibit or reduce expression or production of a target gene involved in a disease process, e.g., for the treatment of a neurodegenerative disease, cancer or atherosclerosis, for example to achieve a therapeutic effect.

In general, invention recombinant vector (e.g., AAV) plasmids, vector genomes, recombinant virus particles, methods and uses may be used to deliver any heterologous polynucleotide (transgene) with a biological effect to treat or ameliorate one or more symptoms associated with any disorder related to insufficient or undesirable gene expression. Invention recombinant vector (e.g., AAV) plasmids, vector genomes, recombinant virus particles, methods and uses may be used to provide therapy for various disease states.

There are a number of inherited diseases in which defective genes are known and have been cloned. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus, invention recombinant vector (e.g., AAV) plasmids, vector genomes, recombinant virus particles, methods and uses permit the treatment of genetic diseases. As used herein, a disease state is treated by partially or wholly remedying the deficiency or imbalance that causes the disease or makes it more severe. The use of site-specific integration of nucleic acid sequences to cause mutations or to correct defects is also possible.

Illustrative disease states include, but are not limited to: cystic fibrosis (and other diseases of the lung), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, Pompe's disease, congestive heart failure, retinal degenerative diseases (choroideremia, Leber's congenital amaurosis, and other diseases of the eye), diseases of solid organs (e.g., brain, liver, kidney, heart), and the like.

In accordance with the invention, treatment methods and uses are provided that include invention recombinant vector (e.g., AAV) plasmids, vector genomes, recombinant virus particles and invention viral particles including vector genomes. Methods and uses of the invention are broadly applicable to diseases amenable to treatment by introducing a gene encoding a protein, or increasing or stimulating gene expression or function, e.g., gene addition or replacement. Methods and uses of the invention are also broadly applicable to diseases amenable to treatment by reducing or decreasing gene expression or function, e.g., gene knockout or reduction of gene expression (gene knockdown).

Non-limiting particular examples of diseases treatable in accordance with the invention include those set forth herein as well as a lung disease (e.g., cystic fibrosis), a blood coagulation or bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, lysosomal storage diseases, a copper or iron accumulation disorders (e.g., Wilson's or Menkes disease) lysosomal acid lipase deficiency, a neurological or neurodegenerative disorder, cancer, type 1 or type 2 diabetes, Gaucher's disease, Hurler's disease, adenosine deaminase deficiency, a metabolic defect (e.g., glycogen storage diseases), a retinal degenerative disease (such as RPE65 deficiency or defect, choroideremia, and other diseases of the eye), and a disease of a solid organ (e.g., brain, liver, kidney, heart).

In addition, invention recombinant vector (e.g., AAV) plasmids, vector genomes, recombinant virus particles, methods and uses may be employed to deliver nucleic acids encoding monoclonal antibodies or fragments thereof to provide beneficial biological effects to treat or ameliorate the symptoms associated with cancers, infectious diseases, and autoimmune diseases such as rheumatoid arthritis.

In one embodiment, a method or use of the invention includes: (a) providing a viral particle comprising an invention vector genome, the vector comprising a heterologous polynucleotide sequence and a filler/stuffer polynucleotide sequence, wherein the heterologous polynucleotide sequence is operably linked to an expression control element conferring transcription of said polynucleotide sequence, such that the combined length has a total length between about 3.0-5.5 Kb, or between about 4.0-5.0 Kb, or between about 4.3-4.8 Kb; and (b) administering an amount of the viral particle to the mammal such that said heterologous polynucleotide is expressed in the mammal. In particular aspects, expression of the heterologous polynucleotide encodes a protein or inhibitory nucleic acid that provides a therapeutic benefit to the mammal (e.g., human).

In another embodiment, a method or use of the invention includes delivering or transferring a heterologous polynucleotide sequence into a mammal or a cell of a mammal, by administering a viral (e.g., AAV) particle or plurality of viral (e.g., AAV) particles comprising an invention vector genome, the vector comprising the heterologous polynucleotide sequence and a filler/stuffer polynucleotide sequence such that the combined length has a total length of between about 3.0-5.5 Kb, or between about 4.0-5.0 Kb, or between about 4.3-4.8 Kb to a mammal or a cell of a mammal, thereby delivering or transferring the heterologous polynucleotide sequence into the mammal or cell of the mammal.

In a further embodiment, a method or use of the invention for treating a mammal deficient in need of protein expression or function includes providing a viral (e.g., AAV) particle or plurality of viral (e.g., AAV) particles comprising an invention vector genome, the vector comprising a heterologous polynucleotide sequence and a filler/stuffer polynucleotide sequence such that the combined length has a total length of between about 3.0-5.5 Kb, or between about 4.0-5.0 Kb, or between about 4.3-4.8 Kb; and administering the viral particle or plurality of viral particles to the mammal, where the heterologous polynucleotide sequence encodes a protein expressed in the mammal, or where the heterologous polynucleotide sequence encodes an inhibitory sequence or protein that reduces expression of an endogenous protein in the mammal.

Methods and uses of the invention include treatment methods, which result in any therapeutic or beneficial effect. In various invention methods and uses, further included are inhibiting, decreasing or reducing one or more adverse (e.g., physical) symptoms, disorders, illnesses, diseases or complications caused by or associated with the disease, such as reduced blood clotting time, reduced administration dosage of supplemental clotting factor protein.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Vector genomes, recombinant virus particles including vector genomes, methods and uses of the invention, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

The vector genome or virus particle (e.g., AAV) dose to achieve a therapeutic effect, e.g., the dose in vector genomes/per kilogram of body weight (vector genomes/ kilogram, vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can readily determine virion dose range to treat a patient having a particular disease or disorder based on the aforementioned factors, as well as other factors. Generally, doses will range from at least $1\times10^8$, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect.

Using hemophilia as an example, generally speaking, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than 5% of normal is needed. With respect to treating such a hemophilic subject, a typical dose is at least $1\times10^{10}$ vector genomes (vg) per kilogram (vg/kg) of the weight of the subject, or between about $1\times10^{10}$ to $1\times10^{11}$ vg/kg of the weight of the subject, or between about $1\times10^{11}$ to $1\times10^{12}$ vg/kg of the weight of the subject, or between about $1\times10^{12}$ to $1\times10^{13}$ vg/kg of the weight of the subject, to achieve a desired therapeutic effect.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) delivery or administration of a vector genome or virus (e.g., AAV) particle of the invention. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a vector genome or virus (e.g., AAV) particle of the invention, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The invention is useful in animals including veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

As set forth herein, invention vectors and virus particles comprising such vectors can be used to provide a protein to a subject where there is an insufficient amount of the protein or a deficiency in a functional gene product (protein), or to provide an inhibitory nucleic acid or protein to a subject who produces an aberrant, partially functional or non-functional gene product (protein) which can lead to disease. Accordingly, subjects appropriate for treatment include those having or at risk of producing an insufficient amount or having a deficiency in a functional gene product (protein), or produce an aberrant, partially functional or non-functional gene product (protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects therefore include subjects that have such defects regardless of the disease type, timing or degree of onset, progression, severity, frequency, or type or duration of symptoms.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for invention methods and uses, but the subject may not manifest the disease. Such subjects therefore include those screened positive for an insufficient amount or a deficiency in a functional gene product (protein), or that produce an aberrant, partially functional or non-functional gene product (protein), which can lead to disease; and subjects that screen positive for an aberrant, or defective (mutant) gene product (protein) that leads to disease, even though such subjects do not manifest symptoms of the disease.

Methods and uses of the invention include delivery and administration systemically, regionally or locally, or by any route, for example, by injection, infusion, orally (e.g., ingestion or inhalation), or topically (e.g., transdermally). Such delivery and administration include intravenously, intramuscularly, intraperitoneally, intradermally, subcutaneously, intracavity, intracranially, transdermally (topical), parenterally, e.g. transmucosally or rectally. Exemplary administration and delivery routes include intravenous (i.v.), intraperitoneal (i.p.), intraarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, intralymphatic.

Doses can vary and depend upon whether the treatment is prophylactic or therapeutic, the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

Recombinant vector (e.g., AAV) plasmids, vector genomes, recombinant virus particles (e.g., AAV) and other compositions, agents, drugs, biologics (proteins) can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle or transformed cell to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and anti-fungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the vector genomes, virus particles (e.g., AAV) and methods and uses of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., AAV) plasmids, vector genomes, recombinant virus particles (e.g., AAV), and pharmaceutical compositions thereof can be packaged in single or multiple unit dosage form for ease of administration and uniformity of dosage.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a vector (e.g., AAV) genome or virus particle (e.g., AAV) and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., a recombinant vector (e.g., AAV) plasmid, vector genome, or recombinant virus particle (e.g., AAV)) are an example of a genus of equivalent or similar features.

As used herein, the singular forms "a", "and," and "the" include plural referents unless the context clearly indicates otherwise. Thus, for example, reference to "a polynucleotide" includes a plurality of such polynucleotides, reference to "a vector" includes a plurality of such vectors, and reference to "a virus" or "particle" includes a plurality of such virions/particles.

As used herein, all numerical values or numerical ranges include integers within such ranges and fractions of the values or the integers within ranges unless the context clearly indicates otherwise. Thus, to illustrate, reference to at least 80% identity, includes 81%, 82%, 83%, 84%, 85%, 86%, 87%, 88%, 89%, 90%, 91%, etc., as well as 81.1%, 81.2%, 81.3%, 81.4%, 81.5%, etc., 82.1%, 82.2%, 82.3%, 82.4%, 82.5%, etc., and so forth.

Reference to a number with more (greater) or less than includes any number greater or less than the reference number, respectively. Thus, for example, a reference to less than 1,000, includes 999, 998, 997, etc. all the way down to the number one (1); and less than 100, includes 99, 98, 97, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as a percentage range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges of 11-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

This example includes a description of various materials and methods.

Standard PCR was performed on plasmid DNA containing AAV vector genome sequence as a positive control for PCR amplification (FIG. 3, Panels A and B,) and on vector genome DNA extracted from the purified vector preparation (FIG. 2, Panels A and C, for vectors with genome sizes 2.7 Kb and 4.2 Kb, respectively) and vector genome DNA extracted after treatment of vector with DNAse I (FIG. 2, Panels B and D, vector genome sizes 2.7 Kb and 4.2 Kb, respectively). A primer located within the transgene cassette sequence (red circle on the figure) was used in each PCR reaction in a pair-combination with a set of primers spanning sequence in transgene cassette and flanking segment of plasmid backbone containing antibiotic resistance (KanR or AmpR) gene. PCR reactions were analyzed using 1% agarose/EtBr gel electrophoresis.

The data for FIG. 3, controls for PCR amplification, plasmid DNA: PCR fragments were generated for all primer pairs (9 primer pairs, Panels A and B) when plasmid DNA was used as a template, suggesting that all primer pairs used in the study generate PCR products. All PCR products were of the expected size as predicted based by plasmid sequence and primer location. As expected, no PCR amplification was observed when plasmid sample was treated with DNase I prior to PCR (Panel C).

The data for FIG. 2: Only a set of primer pairs generated PCR products in experiments when PCR was performed on DNA extracted from the purified vector (6 primer pairs for vector with short, 2.7 Kb, genome (Panels A and B), and 4 primer pairs for vector with long, 4.2 Kb, genome (Panels C and D). The maximum size of PCR product (combined with vector genome sequence outside of PCR amplicon) indicated that the maximum size of amplified DNA corresponds to the packaging capacity of AAV virus (4.5 Kb)

Treatment of vector preparation with DNase I before extraction of DNA from the vector (FIG. 2, Panels B and D) did not alter the PCR amplification patterns (FIG. 2, Panels A and C, compared to Panels B and D, respectively): number of primer pairs generating the PCR product and PCR product sizes did not change suggesting that sequences amplified in PCR (vector genome and flanking sequences) are protected from DNAse, encapcidated.

The size of encapcidated DNA (e.g. DNase-resistant plasmid backbone DNA combined with the vector genome size) was comparable for vectors with short and long genome and approximately corresponded to the packaging capacity of the AAV vector (4.5 Kb). Packaged DNA in vector with short genome included plasmid sequences flanking the genome, indicating that vectors with short genomes package plasmid sequences up to a full packaging capacity of AAV virus.

Example 2

This example includes a description of generating and purifying recombinant AAV vectors using a GMP-comparable manufacturing process.

Levels of residual plasmid DNA were evaluated in a series of AAV2vectors containing single stranded transgene expression cassettes that ranged in size as follows: rAAV A: 2. 7 kb (57% size of wild type); rAAV B: 3. 7 kb (83% of wild type); and rAAV C: 4.3 kb (91% of wild type). Multiple lots of each of the constructs were generated and purified using the same process. Vectors were generated by helper virus free transfection of HEK293 cells, and purified by combined cation exchange chromatography (foros SOHS) and isOQVCnic cesium chloride ultracentrifugation.

Concentration of residual plasmid DNA was measured in KanR copies per mL of vector preparation and then expressed as a % of vector genomes (vg) or pg per 10^9 vg based on the assumption that each KanR (Amp R) copy represents a full plasmid copy (worst case scenario). Vector titers and concentration of residual plasmid DNA were measured by real-time quantitative PCR (aPCR) with TaqMan technology according to the manufacturer protocol using primers and probes specific to KanR or Amp R gene located in the backbone of the transgene plasmid in the close proximity to the 5' ITR of the transgene cassette.

In DNase studies $1\times10^6$ vector genome or plasmid copies were digested with 5U of DNase 1. The amplification was performed by standard PCR using 500 vector genome or plasmid copies per PCR reaction. Plasmid DNA impurities in AAV vectors with short transgene cassettes were DNase resistant indicating encapsidation of plasmid DNA fragments proximal to vector plasmid ITR.

A conservative method was used to quantify residual plasmid DNA based on copy number measure for target qPCR amplicons in vector samples; namely the copy number was multiplied by the Mr of the plasmid. The level of impurities as a function of transgene cassette size is summarized in FIG. 1. The evaluation showed that rAAV A (2.7 kb size) contained 164 pg/$10^9$ vg (n=9) residual plasmid DNA; rAAV B (3.7 kb size) contained 42.7 pg/$10^9$ vg (n 32); and rAAV C (4.3 kb size) contained 14.0 pg/$10^9$ vg (n 29).

Further, vector plasmid 'backbone' DNA packaging occurs to a substantial degree through 'reverse packaging' from ITRs, which is markedly decreased using an oversized (>4.7 bp) backbone (FIG. 5).

Example 3

This example includes a description of studies showing DNA impurities with vector prepared without the oversized backbone compared to vectors prepared using an oversized backbone.

A series of 12 batches of recombinant AAV vectors were prepared using the same methods, based on vector production by transient transfection of human embryonic kidney 293 cells according the following vector production and purification method:

Samples of purified vectors from 9 vector batches prepared using production plasmid vector with an oversized backbone, and three prepared using a production plasmid without the oversized backbone feature, were subjected to measurement of residual host cell plasmid DNA as determined by qPCR measurement of residual levels of the Ampillicin and Kanamicin resistant genes contained in the production plasmid regions that are not intended to be part of the purified vector production (and are hence impurities). The method used for measurement of this impurity is described as follows: Residual Plasmid DNA by Real-Time qPCR The TaqMan® real-time Q-PCR procedure described uses target-specific Q-PCR primers and probe, to detect specific sequences in the production plasmids ($Amp^R$ or $Kan^R$) used for vector production. In cases in which one target was common for all plasmids used in vector manufacture, total residual plasmid was determined in a single qPCR assay. In case in which both $Amp^R$ and $Kan^R$ was present in one or more of the production plasmids for a given batch, total residual plasmid was calculated as a sum of residual $Amp^R$ and residual $Kan^R$ DNA each determined in a separate assay. For each batch reported in this example;

1. Prepared three independent dilutions of the Test Article and Reference vector in Q-PCR dilution buffer;
2. Calculates copy number per well based on the Slope and intercept of the standard curve (Ct vs. LOG (copy number of each standard). Unknown= $10^{(Ct-Intercept)/slope}$. The correlation coefficient (Pearson $R^2$) of the standards reflects the average Ct value for each standard vs. the LOG (copy number of each standard).
3. Calculated amplicon concentration in each of the three Test Article dilutions, each of the three Reference vector dilutions, and Mean concentrations, respectively:

$Amp^R$ or $Kan^R$ [copies/ml]=Mean [copies/well or 5 ul]×200×dilution factor

4. Conversion of copy number concentration to a mass (e.g. pg/mL) may be performed using assumption about the average size of residual plasmid DNA copies.

The resulting level of residual plasmid DNA impurities in the 12 determination shown in FIG. 6 indicated that the average level of 301 pg plasmid DNA impurities per 10^9 vector genomes was 5 fold higher in the vectors prepared using a vector plasmid without (lacking) the oversized backbone compared to the average measured in vectors prepared using an oversized backbone, which was about 60 pg DNA impurities per 10^9 vg. Thus, oversized backbone in vector plasmid can be used to reduce impurities in the viral vector preparation.

What is claimed is:

1. A recombinant vector plasmid comprising a heterologous polynucleotide sequence and a first and second filler or stuffer polynucleotide sequence, wherein said heterologous polynucleotide sequence has a length less than 4.7 Kb, and wherein said first filler or stuffer polynucleotide sequence has a length that when combined with said heterologous polynucleotide sequence the total combined length of the heterologous polynucleotide sequence and first filler or stuffer polynucleotide sequence is between about 3.0-5.5 Kb, between about 4.0-5.0 Kb, or between about 4.3-4.8 Kb, wherein said first filler or stuffer polynucleotide sequence is not a bacterial polynucleotide sequence or an intron, wherein said second filler or stuffer polynucleotide sequence is inert and is positioned outside of two adeno-associated virus (AAV) ITR sequences, and wherein said second stuffer or filler sequence has a length of 7.0-10.0 Kb.

2. The recombinant vector plasmid of claim 1, wherein said first filler or stuffer polynucleotide sequence has a length between about 4.0-5.0 Kb, between about 4.5-5.0 Kb, between about 4.0-5.2 Kb, or between about 4.3-4.8 Kb.

3. The recombinant vector plasmid of claim 1, wherein the vector plasmid comprises an adeno-associated virus (AAV) vector.

4. The recombinant vector plasmid of claim 1, wherein the heterologous polynucleotide sequence and said first filler or stuffer polynucleotide sequence comprises a vector genome capable of being packaged or encapsidated into a viral particle or an adeno-associated virus (AAV) particle.

5. The recombinant vector plasmid of claim 1, wherein the heterologous polynucleotide sequence comprises a vector genome capable of being packaged or encapsidated into a viral particle or an adeno-associated virus (AAV) particle, and the full-length second filler or stuffer polynucleotide sequence is not packaged or encapsidated into a viral particle or an adeno-associated virus (AAV) particle.

6. The recombinant vector plasmid of claim 1, wherein said first filler or stuffer polynucleotide sequence is positioned within the heterologous polynucleotide sequence.

7. The recombinant vector plasmid of claim 1, wherein said first or second filler or stuffer polynucleotide sequence comprises a sequence that is distinct from any of: the heterologous polynucleotide sequence, an AAV inverted terminal repeat (ITR) sequence, an expression control element, an origin of replication, a selectable marker or a poly-Adenine sequence.

8. The recombinant vector plasmid of claim 1, wherein said first or second filler or stuffer polynucleotide sequence comprises a sequence of about 1-10, 10-20, 20-30, 30-40, 40-50, 50-60, 60-75, 75-100, 100-150, 150-200, 200-250, 250-300, 300-400, 400-500, 500-750, 750-1,000, 1,000-1, 500, 1,500-2,000, 2,000-2,500, 2,500-3,000, 3,000-3,500, 3,500-4,000, 4,000-4,500, or 4,500-5,000 nucleotides in length.

9. The recombinant vector plasmid of claim 1, wherein said heterologous polynucleotide sequence encodes a therapeutic protein.

10. The vector of claim 9, wherein said therapeutic protein comprises a blood clotting factor.

11. The vector of claim 9, wherein said therapeutic protein comprises CFTR (cystic fibrosis transmembrane regulator protein), Factor XIII, Factor IX, Factor X, Factor VIII, Factor VIIa, or protein C, an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes, or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

12. The recombinant vector plasmid of claim 1, wherein said heterologous polynucleotide sequence comprises a polynucleotide which, when transcribed, is transcribed into RNA.

13. The recombinant vector plasmid of claim 1, wherein said heterologous polynucleotide sequence comprises a polynucleotide which, when transcribed, is transcribed into an inhibitory nucleic acid (e.g., inhibitory RNA).

14. The recombinant vector plasmid of claim 13, wherein said inhibitory nucleic acid comprises a single-stranded sequence, or forms a double- or triple-stranded sequence.

15. The recombinant vector plasmid of claim 13, wherein said inhibitory nucleic acid comprises micro-RNA (miRNA), siRNA, shRNA, trans-splicing RNA, antisense RNA or triplex forming RNA.

16. The recombinant vector plasmid of claim 13, wherein said inhibitory nucleic acid inhibits expression of: huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular oedma (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; mutant rhodopsin gene (RHO) in autosomal dominantly inherited retinitis pigmentosa (adRP); or wherein said inhibitory nucleic acid binds to a transcript of any of the foregoing genes or sequences.

17. The recombinant vector plasmid of claim 1, further comprising an expression control sequence that drives transcription of the heterologous polynucleotide sequence.

18. The recombinant vector plasmid of claim 17, wherein the expression control sequence comprises a promoter or enhancer that contributes to transcription of the heterologous polynucleotide sequence.

19. The recombinant vector plasmid of claim 17, wherein the expression control element comprises a constitutive or regulatable control element.

20. The recombinant vector plasmid of claim 17, wherein the expression control element comprises a tissue-specific expression control element or promoter.

21. The recombinant vector plasmid of claim 1, further comprising a poly-Adenine sequence located 3' of the heterologous polynucleotide sequence.

22. The recombinant vector plasmid of claim 1, further comprising a selectable marker and/or an origin of replication.

23. The recombinant vector plasmid of claim 22, wherein said selectable marker comprises a gene encoding a protein that provides antibiotic resistance.

24. A cell comprising the recombinant vector plasmid of claim 1.

25. A method of producing recombinant viral or AAV particles, comprising:
  a. introducing into a packaging helper cell a recombinant vector plasmid of claim 1, to produce a productive viral or AAV infection; and
  b. culturing said helper cells under conditions to produce recombinant viral or AAV particles having vector genome.

26. A method of producing recombinant viral or AAV particles, with reduced amounts of recombinant viral or AAV particles in which the recombinant vector genomes include contaminating nucleic acid, comprising
  a. introducing into a packaging helper cell a recombinant vector plasmid of claim 1; and
  b. culturing said helper cells under conditions to produce recombinant viral or AAV particles having a vector genome, wherein the recombinant viral or AAV particles produced have reduced numbers of viral or AAV particles with recombinant vector genomes that contain contaminating nucleic acid compared to the numbers of viral or AAV particles that contain contaminating nucleic acid produced under conditions in which the filler or stuffer polynucleotide sequence is absent from the recombinant vector plasmid.

27. The method of claim 26, wherein said contaminating nucleic acid comprises nucleic acid derived from backbone or plasmid portion of a recombinant vector plasmid.

28. The method of claim 26, wherein said contaminating nucleic acid comprises bacterial sequences or sequences other than the heterologous polynucleotide sequence, or ITR, promoter, enhancer, origin of replication, poly-Adenine sequence, or selectable marker.

29. The cell of claim 24, wherein the cell comprises mammalian cells.

30. The cell of claim 24, wherein the cell provides helper functions that package said vector into a viral particle.

31. The cell of claim 24, wherein the cell provides AAV helper functions.

32. The cell of claim 24, wherein the cell provides AAV Rep and/or Cap proteins.

33. The vector of claim 7, wherein said ITR sequences are derived from AAV1, AAV2, AAV3, AAV4, AAV5, AAV6, AAV7, AAV8, AAV9, AAV10, AAV11, Rh74, Rh10 serotype, or a hybrid or chimera of any of the foregoing AAV serotypes.

* * * * *